(12) United States Patent
Masciotti et al.

(10) Patent No.: US 10,869,624 B2
(45) Date of Patent: Dec. 22, 2020

(54) REAL TIME ASSESSEMENT OF SENSOR PERFORMANCE AND PREDICTION OF THE END OF THE FUNCTIONAL LIFE OF AN IMPLANTED SENSOR

(71) Applicant: Senseonics, Incorporated, Germantown, MD (US)

(72) Inventors: James Masciotti, Germantown, MD (US); Andrew Dehennis, Germantown, MD (US); Xiaoxiao Chen, Washington, DC (US); Barkha Raisoni, Germantown, MD (US); Barbara Montgomery, Gaithersburg, MD (US)

(73) Assignee: Senseonics, Incorporated, Germantown, MD (US)

( * ) Notice: Subject to any disclaimer, the term of this patent is extended or adjusted under 35 U.S.C. 154(b) by 520 days.

(21) Appl. No.: 15/786,954

(22) Filed: Oct. 18, 2017

(65) Prior Publication Data

US 2018/0103879 A1  Apr. 19, 2018

Related U.S. Application Data

(60) Provisional application No. 62/409,551, filed on Oct. 18, 2016.

(51) Int. Cl.
*A61B 5/1495* (2006.01)
*A61M 5/172* (2006.01)
(Continued)

(52) U.S. Cl.
CPC .......... *A61B 5/1495* (2013.01); *A61B 5/0024* (2013.01); *A61B 5/0031* (2013.01);
(Continued)

(58) Field of Classification Search
CPC . A61B 5/14532; A61B 5/1495; A61B 5/0031; A61B 5/0247; A61B 5/145;
(Continued)

(56) References Cited

U.S. PATENT DOCUMENTS 6,895,263 B2  5/2005  Shin et al.
8,515,516 B2  8/2013  Kamath et al.
(Continued)

FOREIGN PATENT DOCUMENTS

EP  2 335 584 A2  6/2011
EP  2 305 105 B1  5/2012
(Continued)

*Primary Examiner* — Eric F Winakur
(74) *Attorney, Agent, or Firm* — Rothwell, Figg, Ernst & Manbeck, P.C.

(57) ABSTRACT

An analyte monitoring system and method. The analyte monitoring system may include an analyte sensor and a transmitter. The analyte sensor may include an indicator element that exhibits one or more detectable properties based on an amount or concentration of an analyte in proximity to the indicator element. The transmitter may be configured to receive measurement information from the analyte sensor. The transmitter may be configured to assess in real time a performance of the analyte sensor based on at least the measurement information. The transmitter may be configured to determine whether the performance of the analyte sensor is deficient based at least on the assessed performance of the analyte sensor. The transmitter may be configured to predict an amount of time remaining before the performance of the analyte sensor becomes deficient based on at least the assessed performance of the analyte sensor.

17 Claims, 26 Drawing Sheets

(51) Int. Cl.
  *A61B 5/145* (2006.01)
  *A61M 5/142* (2006.01)
  *A61B 5/00* (2006.01)

(52) U.S. Cl.
  CPC .......... *A61B 5/0062* (2013.01); *A61B 5/0075* (2013.01); *A61B 5/14532* (2013.01); *A61M 5/14244* (2013.01); *A61M 5/1723* (2013.01); *A61B 2560/028* (2013.01); *A61B 2560/0223* (2013.01); *A61B 2560/0247* (2013.01); *A61B 2560/0271* (2013.01); *A61B 2560/0276* (2013.01); *A61M 2205/3576* (2013.01); *A61M 2205/50* (2013.01)

(58) Field of Classification Search
  CPC .............. A61B 5/14503; A61B 5/7221; A61B 2560/0271; A61B 2560/028; A61B 2560/0223
  USPC .......................................... 600/309, 345–366
  See application file for complete search history.

(56) References Cited

U.S. PATENT DOCUMENTS

| | | | |
|---|---|---|---|
| 9,211,092 B2 | 12/2015 | Bhavaraju et al. | |
| 9,289,179 B2 | 5/2016 | Hayter et al. | |
| 9,736,210 B2 | 8/2017 | Root et al. | |
| 9,743,872 B2 | 8/2017 | Hayter et al. | |
| 9,833,199 B2 | 12/2017 | Johnson et al. | |
| 9,949,678 B2 | 4/2018 | Fennell et al. | |
| 10,111,609 B2 | 10/2018 | Schmelzeisen-Redeker et al. | |
| 2007/0016381 A1 | 1/2007 | Kamath et al. | |
| 2008/0300572 A1* | 12/2008 | Rankers | G16H 40/63 604/504 |
| 2010/0169035 A1* | 7/2010 | Liang | A61B 5/14865 702/65 |
| 2011/0004085 A1 | 1/2011 | Mensinger et al. | |
| 2012/0165636 A1 | 6/2012 | Feldman et al. | |
| 2012/0238842 A1 | 9/2012 | Colvin, Jr. et al. | |
| 2013/0303869 A1 | 11/2013 | Rebec et al. | |
| 2013/0331667 A1 | 12/2013 | Colvin, Jr. et al. | |
| 2014/0141524 A1 | 5/2014 | Keith | |
| 2014/0182350 A1* | 7/2014 | Bhavaraju | G01M 99/008 73/1.02 |
| 2015/0253334 A1 | 9/2015 | Johnson et al. | |
| 2015/0351670 A1* | 12/2015 | Vanslyke | A61B 5/1495 600/301 |

FOREIGN PATENT DOCUMENTS

| | | |
|---|---|---|
| EP | 2 329 770 B1 | 9/2014 |
| EP | 1 942 801 B1 | 10/2018 |
| WO | 03/094714 A1 | 11/2003 |

\* cited by examiner

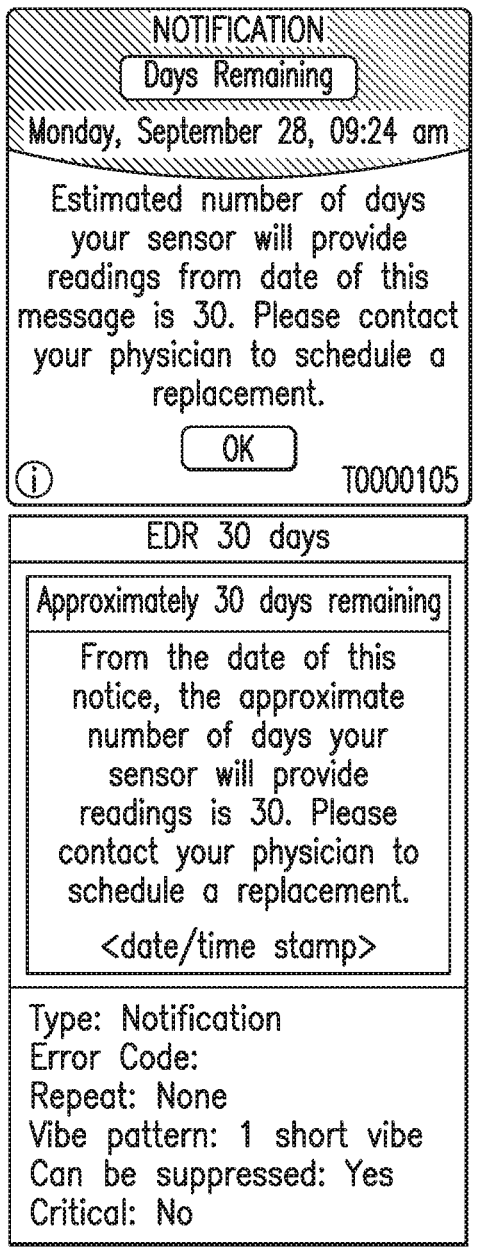
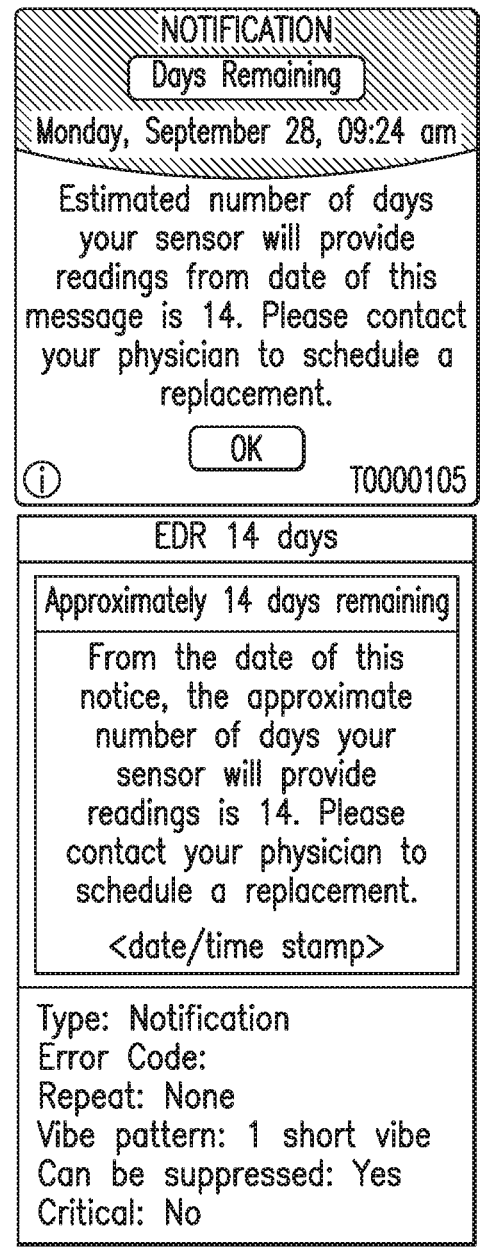
FIG. 7A
FIG. 7B

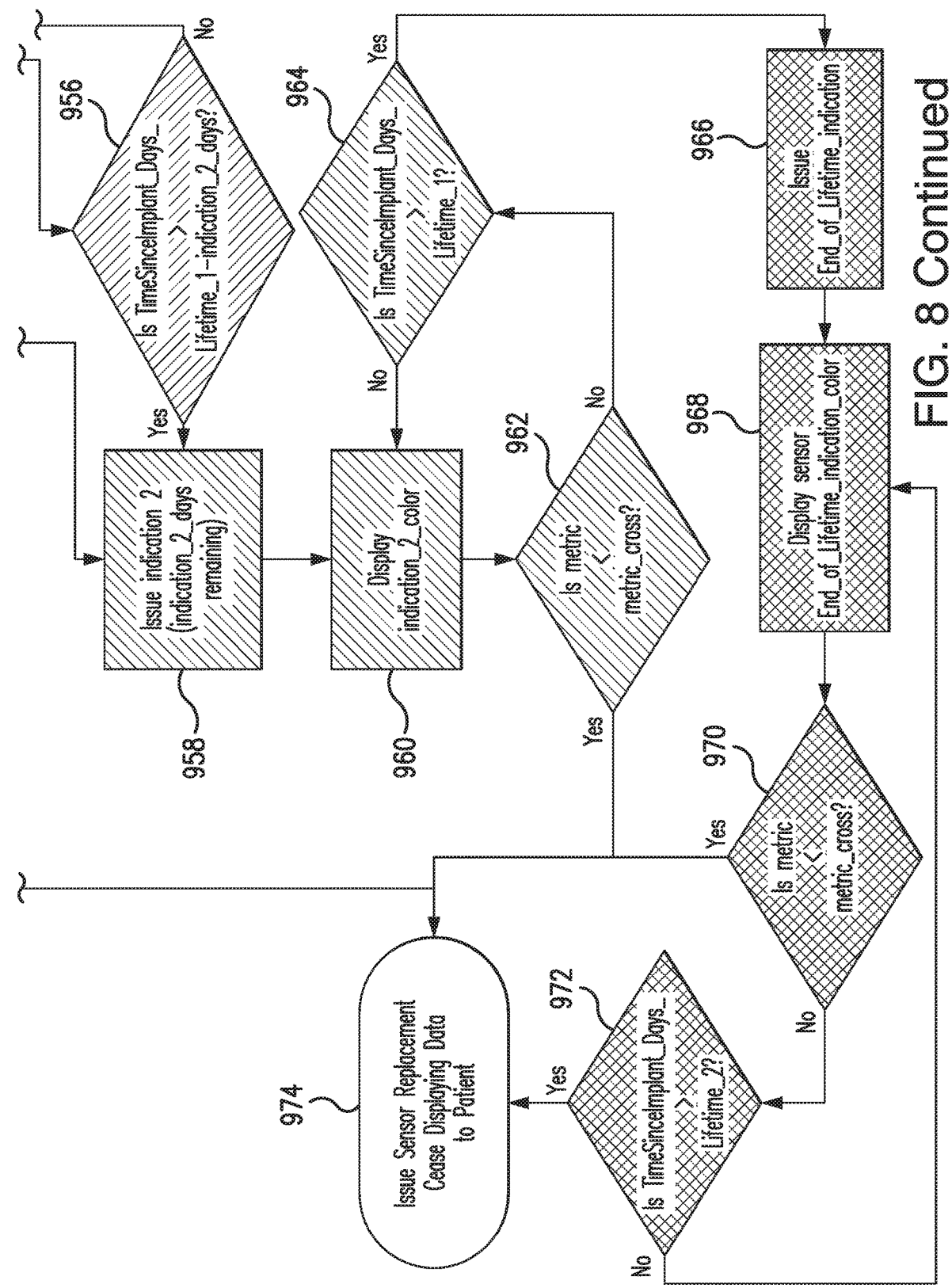

Days Remaining Reminder

Alarm History

ALL

Wednesday, March 11, 2015

| Days Remaining | 10:18 PM > |
| Calibrate Now | 08:54 PM > |
| Days Remaining | 08:34 PM > |
| Rate Rising | 02:59 PM > |
| Days Remaining | 05:13 AM > |

Tuesday, March 10, 2015

| Calibrate Now | 11:13 PM > |
| Low Glucose | 09:19 PM > |

▲
Wed 11 March, 2015

FIG. 20

REAL TIME ASSESSEMENT OF SENSOR PERFORMANCE AND PREDICTION OF THE END OF THE FUNCTIONAL LIFE OF AN IMPLANTED SENSOR

CROSS-REFERENCE TO RELATED APPLICATION

The present application claims the benefit of priority to U.S. Provisional Application Ser. No. 62/409,551, filed on Oct. 18, 2016, which is incorporated herein by reference in its entirety.

BACKGROUND

Field of Invention

Aspects of the present invention relate to assessing in real time sensor performance, determining whether sensor performance is no longer suitable for continuous analyte monitoring, detecting sensor delamination, and predicting the end of the functional life of an implanted sensor. The end of life prediction may be based on one or more of real time assessment of sensor performance and the body's response to the implanted sensor.

Discussion of the Background

Conventional systems including devices implanted (fully or partially) in the body of an animal (e.g., a human) are unable to predict with accuracy the end of the functional lifetime the implanted device.

SUMMARY

The manner in which a body (e.g., a human body) responds to a device (e.g., an analyte sensor, an insulin pump, or a pacemaker) implanted (fully or partially) in the body may vary widely from body to body. That is, the body's response to an implanted device may vary on a patient by patient basis. This variable response of a body to an implanted device may prevent one from knowing before implant what the lifetime of an implantable device will be and may make accurate prediction of the end of the life of an implanted device difficult. Because different implanted devices will have varying amounts of functional lifetime based on of the body's response to the implant, aspects of the invention may utilize information on a device, the device's performance, and/or the body's response to the device in order to predict the device's functional lifetime.

One aspect of the invention may provide an analyte monitoring system that includes an analyte sensor and a transmitter. The analyte sensor may include an indicator element that exhibits one or more detectable properties based on an amount or concentration of an analyte in proximity to the indicator element. The transmitter may be configured to (i) receive measurement information from the analyte sensor, (ii) assess in real time a performance of the analyte sensor based on at least the measurement information, (iii) determine whether the performance of the analyte sensor is deficient based at least on the assessed performance of the analyte sensor, and/or (iv) predict an amount of time remaining before the performance of the analyte sensor becomes deficient based on at least the assessed performance of the analyte sensor.

Another aspect of the invention may provide a method. The method may include receiving measurement information from an analyte sensor. The analyte sensor may include an indicator element that exhibits one or more detectable properties based on an amount or concentration of an analyte in proximity to the indicator element. The method may include assessing in real time a performance of the analyte sensor based on at least the measurement information. The method may include determining whether the performance of the analyte sensor is deficient based at least on the assessed performance of the analyte sensor. The method may include predicting an amount of time remaining before the performance of the analyte sensor becomes deficient based on at least the assessed performance of the analyte sensor.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 7A-7D illustrate non-limiting examples of indications of the predicted amount of time remaining before sensor end of life, which may be displayed by a display device of the analyte monitoring system in accordance with some non-limiting embodiments.

FIGS. 9A-21 illustrate non-limiting examples of ways in which indications of the predicted amount of time remaining before sensor EOL (or time since implant) may be displayed by a display device of the analyte monitoring system in accordance with some non-limiting embodiments.

DETAILED DESCRIPTION OF PREFERRED EMBODIMENTS

Figure 1:
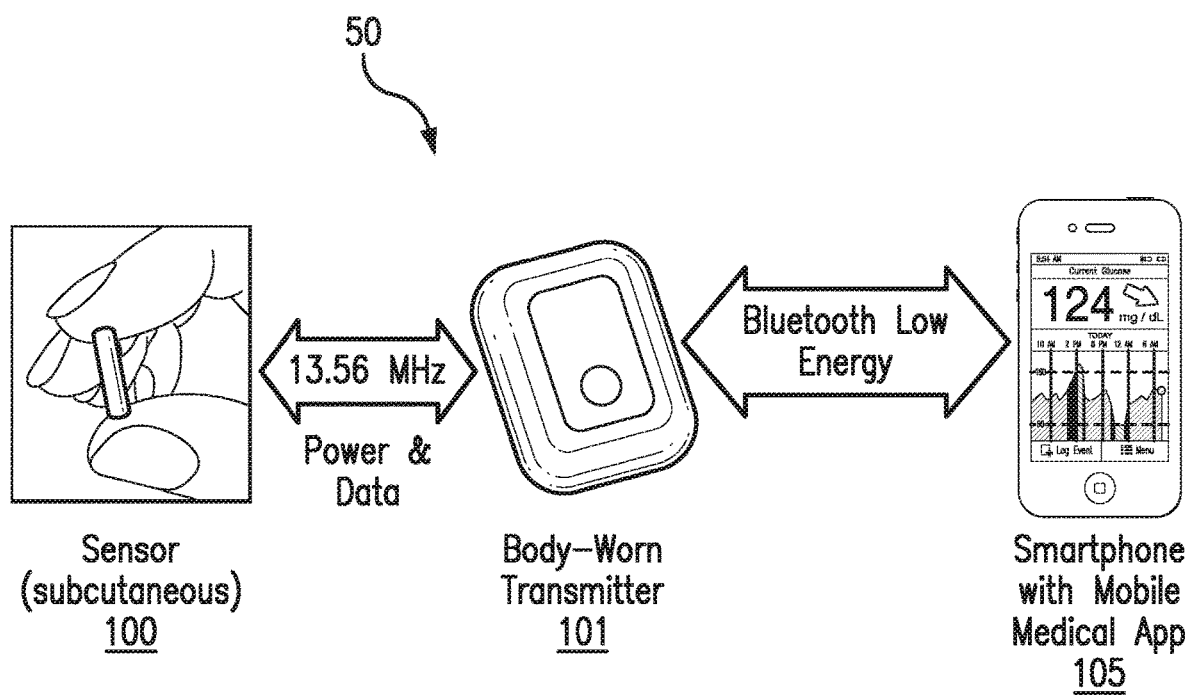
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transmitter 101, and a display device 105. In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transmitter 101 may be an externally worn transmitter (e.g., attached via an armband, wristband, waistband, or adhesive patch). In some embodiments, the transmitter 101 may remotely power and/or communicate with the sensor to initiate and receive the measurements (e.g., via near field communication (NFC)). However, this is not required, and, in some alternative embodiments, the transmitter 101 may power and/or communicate with the sensor 100 via one or more wired connections. In some non-limiting embodiments, the transmitter 101 may be a smartphone (e.g., an NFC-enabled smartphone). In some embodiments, the transmitter 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, information can be downloaded from the transmitter 101 through a Universal Serial Bus (USB) port. In some embodiments, the analyte monitoring system 50 may include a web interface for plotting and sharing of uploaded data.

Figure 2:
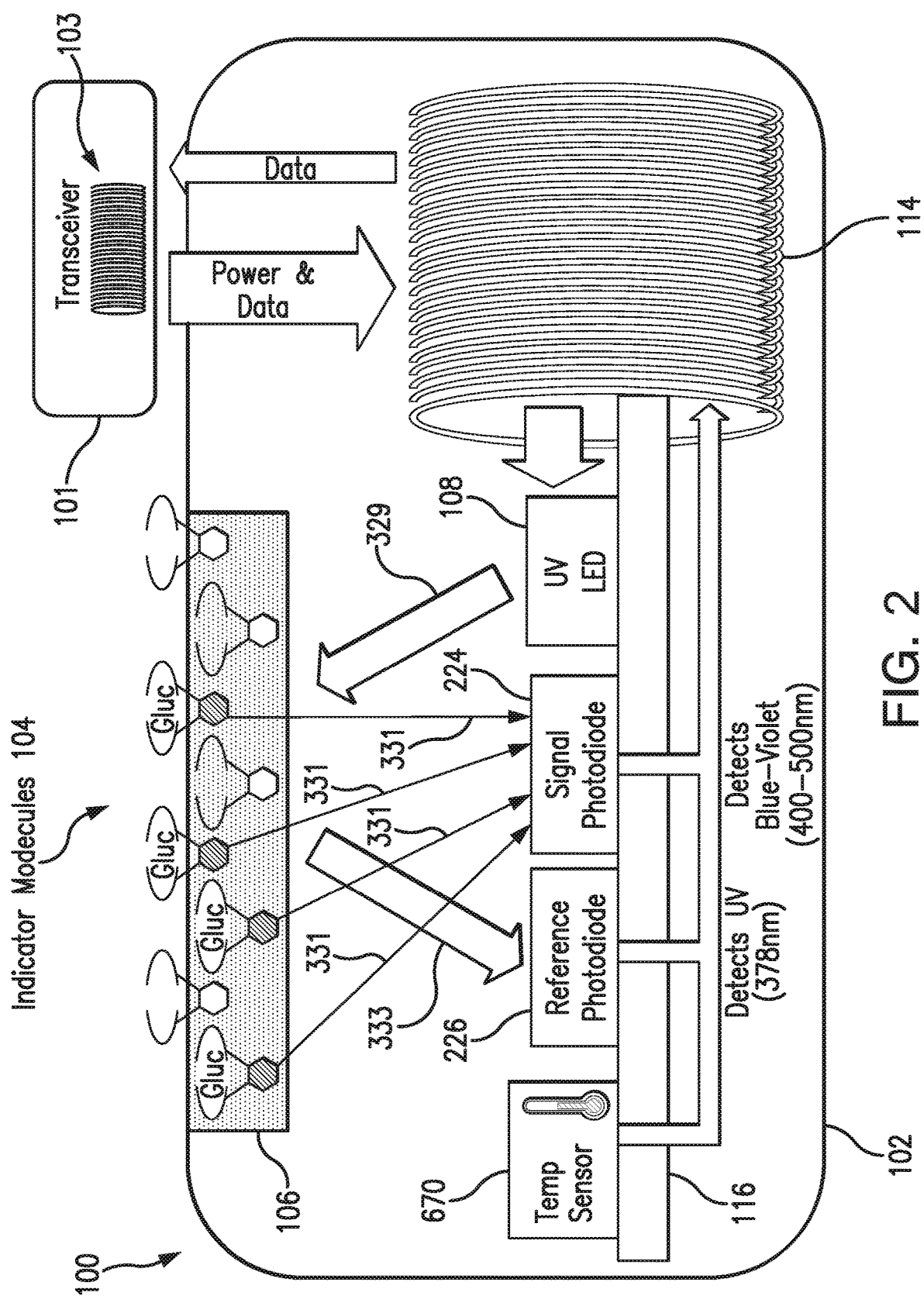
FIG. 2 is a schematic view illustrating a sensor and transmitter of an analyte monitoring system embodying aspects of the present invention.

In some embodiments, as illustrated in FIG. 2, the transmitter 101 may include an inductive element 103, such as, for example, a coil. The transmitter 101 may generate an electromagnetic wave or electrodynamic field (e.g., by using a coil) to induce a current in an inductive element 114 of the sensor 100, which powers the sensor 100. The transmitter 101 may also convey data (e.g., commands) to the sensor 100. For example, in a non-limiting embodiment, the transmitter 101 may convey data by modulating the electromagnetic wave used to power the sensor 100 (e.g., by modulating the current flowing through a coil 103 of the transmitter 101). The modulation in the electromagnetic wave generated by the transmitter 101 may be detected/extracted by the sensor 100. Moreover, the transmitter 101 may receive data (e.g., measurement information) from the sensor 100. For example, in a non-limiting embodiment, the transmitter 101 may receive data by detecting modulations in the electromagnetic wave generated by the sensor 100, e.g., by detecting modulations in the current flowing through the coil 103 of the transmitter 101.

The inductive element 103 of the transmitter 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters (e.g., bandpass filter 112 of FIG. 6) that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/ or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transmitter 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transmitter 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transmitter 101 may communicate using one or more wires connected between the transmitter 101 and the transmitter transcutaneous needle that includes the sensor 100. For another example, in some alternative embodiments, the sensor 100 may be located in a catheter (e.g., for intravenous blood glucose monitoring) and may communicate (wirelessly or using wires) with the transmitter 101.

In some embodiments, the sensor 100 may include a transmitter interface device. In some embodiments where the sensor 100 includes an antenna (e.g., inductive element 114), the transmitter interface device may include the antenna (e.g., inductive element 114) of sensor 100. In some of the transcutaneous embodiments where there exists a wired connection between the sensor 100 and the transmitter 101, the transmitter interface device may include the wired connection.

Figure 3:
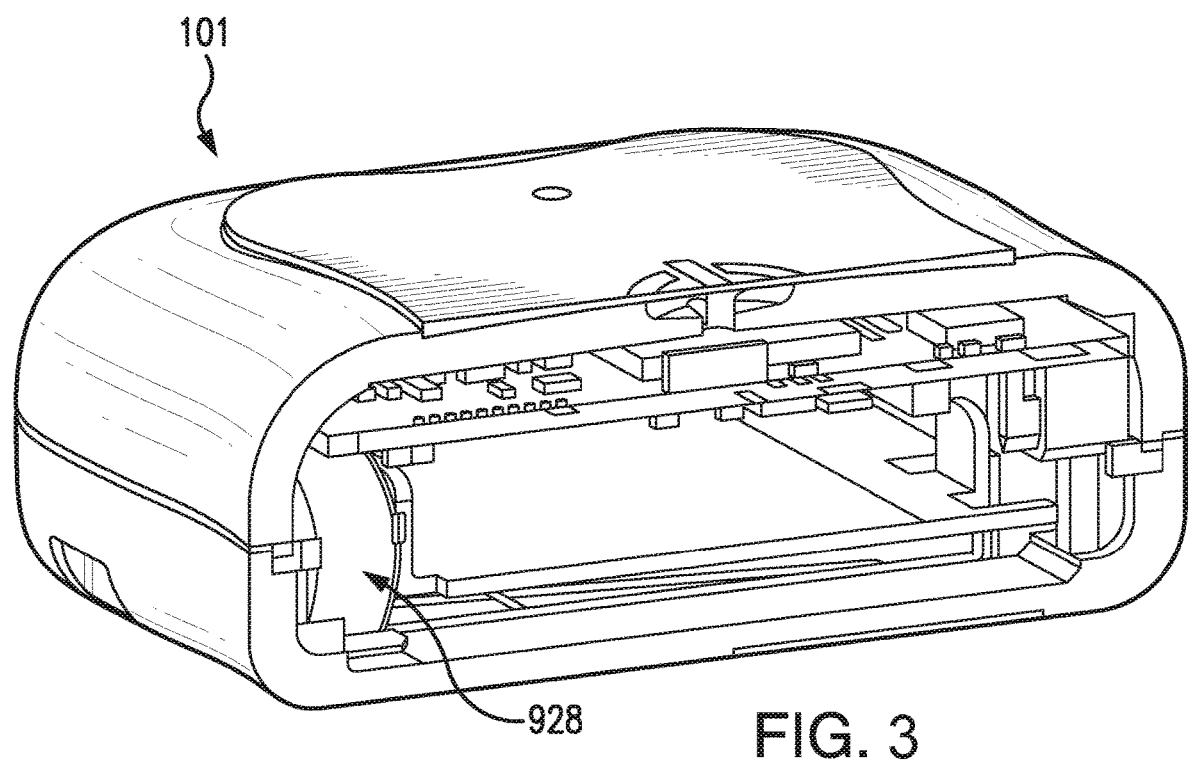
FIG. 3 is cross-sectional, perspective view of a transmitter embodying aspects of the invention.
Figure 4:
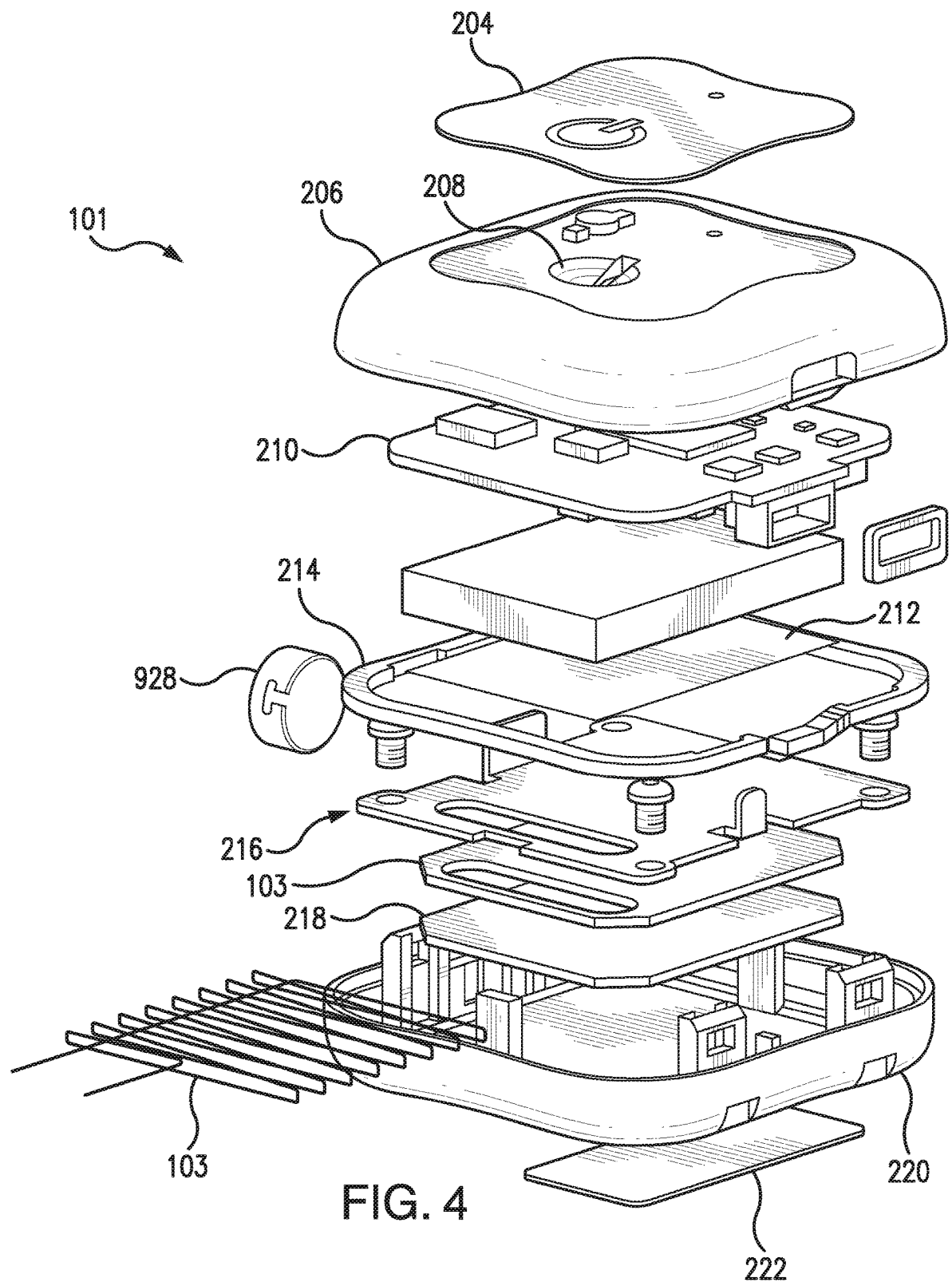
FIG. 4 is an exploded, perspective view of a transmitter embodying aspects of the invention.

FIGS. 3 and 4 are cross-sectional and exploded views, respectively, of a non-limiting embodiment of the transmitter 101, which may be included in the analyte monitoring system illustrated in FIG. 1. As illustrated in FIG. 4, in some non-limiting embodiments, the transmitter 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transmitter electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transmitter assembly process may be performed at one or more electronics houses, which may be internal, external, or a combination thereof. In some embodiments, the assembled transmitter 101 may be programmed and functionally tested. In some embodiments, assembled transmitters 101 may be packaged into their final shipping containers and be ready for sale.

In some embodiments, as illustrated in FIGS. 3 and 4, the antenna 103 may be contained within the housing 206 and 220 of the transmitter 101. In some embodiments, the antenna 103 in the transmitter 101 may be small and/or flat so that the antenna 103 fits within the housing 206 and 220 of a small, lightweight transmitter 101. In some embodiments, the antenna 103 may be robust and capable of resisting various impacts. In some embodiments, the transmitter 101 may be suitable for placement, for example, on an abdomen area, upper-arm, wrist, or thigh of a patient body. In some non-limiting embodiments, the transmitter 101 may be suitable for attachment to a patient body by means of a biocompatible patch. Although, in some embodiments, the antenna 103 may be contained within the housing 206 and 220 of the transmitter 101, this is not required, and, in some alternative embodiments, a portion or all of the antenna 103 may be located external to the transmitter housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
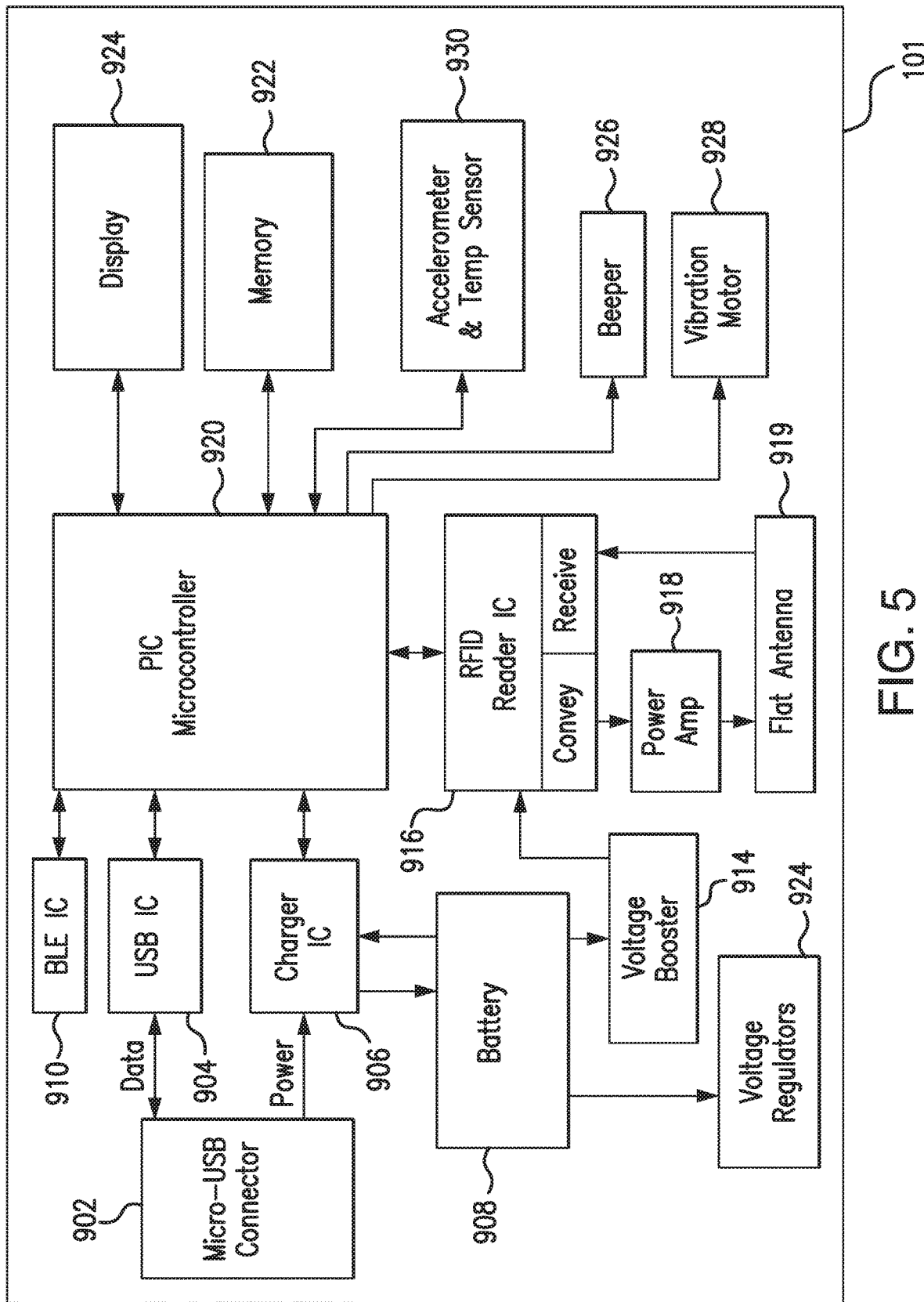
FIG. 5 is a schematic view illustrating a transmitter embodying aspects of the present invention.

FIG. 5 is a schematic view of an external transmitter 101 according to a non-limiting embodiment. In some embodiments, the transmitter 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transmitter 101 may exchange data to and from the external device through the connector 902 and/or may receive power through the connector 902. The transmitter 101 may include a connector integrated circuit (IC) 904, such as, for example, a USB-IC, which may control transmission and receipt of data through the connector 902. The transmitter 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transmitter 101 may include one or more connectors in addition to (or as an alternative to) Micro-USB connector 904. For example, in one alternative embodiment, the transmitter 101 may include a spring-based connector (e.g., Pogo pin connector) in addition to (or as an alternative to) Micro-USB connector 904, and the transmitter 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transmitter 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transmitter 101. However, this is not required, and, in alternative embodiments, all or a portion of the antenna of the wireless communication IC 910 may be external to the transmitter housing.

In some embodiments, the transmitter 101 may include a display interface device, which may enable communication by the transmitter 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transmitter 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transmitter 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transmitter 101 may be in any configuration that permits adequate field strength to be achieved when brought within adequate physical proximity to the inductive element 114 of the sensor 100. In some embodiments, the transmitter 101 may include a power amplifier 918 to amplify the signal to be conveyed by the inductive element 103 to the sensor 100.

The transmitter 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transmitter 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transmitter 101 may include a sensor interface device, which may enable communication by the transmitter 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transmitter 101 (e.g., transcutaneous embodiments), the sensor interface device may include the wired connection.

In some embodiments, the transmitter 101 may include a display 924 (e.g., liquid crystal display and/or one or more light emitting diodes), which PIC microcontroller 920 may control to display data (e.g., analyte concentration values). In some embodiments, the transmitter 101 may include a speaker 926 (e.g., a beeper) and/or vibration motor 928, which may be activated, for example, in the event that an alarm condition (e.g., detection of a hypoglycemic or hyperglycemic condition) is met. The transmitter 101 may also include one or more additional sensors 930, which may include an accelerometer and/or temperature sensor, that may be used in the processing performed by the PIC microcontroller 920.

In some embodiments, the transmitter 101 may be a body-worn transmitter that is a rechargeable, external device worn over the sensor implantation or insertion site. The transmitter 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transmitter 101 may be placed using an adhesive patch or a specially designed strap or belt. The external transmitter 101 may read measured analyte data from a subcutaneous sensor 100 (e.g., up to a depth of 2 cm or more). The transmitter 101 may periodically (e.g., every 2, 5, or 10 minutes) read sensor data and calculate an analyte concentration and an analyte concentration trend. From this information, the transmitter 101 may also determine if an alert and/or alarm condition exists, which may be signaled to the user (e.g., through vibration by vibration motor 928 and/or an LED of the transmitter's display 924 and/or a display of a display device 105). The information from the transmitter 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transmitter 101. In one embodiment, the MMA may be configured to provide push notifications. In some embodiments, the transmitter 101 may have a power button (e.g., button 208) to allow the user to turn the device on or off, reset the device, or check the remaining battery life. In some embodiments, the transmitter 101 may have a button, which may be the same button as a power button or an additional button, to suppress one or more user notification signals (e.g., vibration, visual, and/or audible) of the transmitter 101 generated by the transmitter 101 in response to detection of an alert or alarm condition.

In some embodiments, the transmitter 101 of the analyte monitoring system 50 receives raw signals indicative of an amount or concentration of an analyte in proximity to the analyte indicator element 106 of the analyte sensor 100. In some embodiments, the transmitter 101 may receive the raw signals from the sensor 100 periodically (e.g., every 5, 10, or 20 minutes). In some embodiments, the raw signals may include one or more analyte measurements (e.g., one or more measurements indicative of the level of emission light 331 from the indicator molecules 104 as measured by the photodetector 224) and/or one or more temperature measurements (e.g., as measured by the temperature transducer 670). In some embodiments, the transmitter 101 may use the received raw signals to calculate analyte concentration. In some embodiments, the transmitter 100 may store one or more calculated analyte concentrations (e.g., in memory 922). In some embodiments, the transmitter 100 may convey one or more calculated analyte concentrations to the display device 105.

In some embodiments, the analyte monitoring system 50 may calibrate the conversion of raw signals to analyte concentration. In some embodiments, the calibration may be performed approximately periodically (e.g., every 12 or 24 hours). In some embodiments, the calibration may be performed using one or more reference measurements (e.g., one or more self-monitoring blood glucose (SMBG) measurements), which may be entered into the analyte monitoring system 50 using the user interface of the display device 105. In some embodiments, the transmitter 101 may receive the one or more reference measurements from the display device 105 and perform the calibration.

In some embodiments, the analyte monitoring system 50 may assess in real time the performance of the analyte sensor 100. In some embodiments, circuitry of the transmitter 101 (e.g., the PIC microcontroller 920) may perform the real time assessment of the analyte sensor 100. In some embodiments, the real-time assessment of sensor performance may provide an objective reference to quantify the sensor performance in real time. In some embodiments, the transmitter 101 may assess the in-vivo sensor performance in real time and determine whether the performance of the analyte sensor 100 is suitable for continuous analyte monitoring. In some embodiments, the analyte monitoring system 50 may trigger one or more of a sensor instability alarm and a sensor retirement alarm if the sensor performance is unsuitable for continuous analyte monitoring. In some embodiments, the analyte monitoring system 50 may detect sensor delamination.

In some embodiments, the analyte monitoring system 50 may assess the performance of the analyte sensor 100 at each calibration point (e.g., approximately every 12 or 24 hours). In some embodiments, assessing the performance of the analyte sensor 100 may include calculating a metric for real time assessment of sensor performance (MSP). In some embodiments, the MSP may reflect the real time sensor performance and may be used to determine a sensor performance deficiency and/or to trigger a sensor retirement alarm. In some embodiments, the MSP may take into account measures of one or more of responsivity (e.g., the responsiveness of the analyte indicator element 106 of the sensor 100 to changes in analyte concentration), signal strength (e.g., normalized signal), sensor accuracy (e.g., normMARD), and the body's response to the implant (e.g., normLC). In some embodiments, the MSP may additionally or alternatively take into account measures of one or more of degraded indicator species, reactive oxygen species, and other indications of the status of the sensor. In some embodiments, the MSP may additionally or alternatively take into account the time-based rates of change of the measures.

In some embodiments, the MSP may be the minimum value of one or more measures. In some embodiments, the measures may include one or more of the responsivity, normalized signal, normMARD, and normLc, which are described in detail below. In some embodiments, the measures may additionally or alternatively include indications of degraded indicator species and/or reactive oxygen species. In some embodiments, one or more of the measures may be weighted.

In some embodiments, the MSP may be not a number (NaN) if at least one of the measures/components is NaN. In some non-limiting embodiments, the MSP may be defined as:

$$MSP = \begin{cases} \text{the minimum value of the weighted responsivity,} \\ \text{normalized signal, } normMARD \text{ and } normLc \\ NaN \text{ (not a number), if at least one of} \\ \text{the components is } NaN \end{cases},$$

In some embodiments, the smaller the MSP is, the worse the performance of the sensor is. In some non-limiting embodiments, the weights for one or more of the responsivity, normalized signal, normMARD and normLc may be specified as, for example and without limitation, 2, 1, 99999, and 4, respectively. However, this is not required, and, in some alternative embodiments, the transmitter 101 may use different weights. In some embodiments, these weights may be be optimized for different sensor configurations. In some embodiments, the smaller the weight for a parameter is, the more influence the parameter has on the sensor performance.

In some non-limiting embodiments, the transmitter 101 may calculate MSP and then pass the calculated value through a filter because the calculated MSP may contain noise introduced by errors in calibration points. In some embodiments, the filter may be a Kalman Filter. In some non-limiting embodiments, the transmitter 101 may use a Kalman Filter similar to the one described at http://www.cs.unc.edu/~welch/kalman/kalmanIntro.html, except that the measurement noise R may be set equal to $R_0$. In some non-limiting embodiments, $R_0$ may be equal to, for example and without limitation, 3. In some embodiments, the rest parameter update may follow a standard Kalman Filter procedure. In some embodiments, the Kalman-filtered MSP may be an initial value of 1 (i.e., the filtered MSP may always start with 1 at the very beginning of the sensor life). In some embodiments, if the obtained MSP is NaN, the Kalman Filter may make its output equal to the previously filtered MSP.

In some embodiments, the transmitter 101 may store filtered MSP values (e.g., in memory 922). In some non-limiting embodiments, the transmitter 101 may convey the latest filtered MSP to the analyte sensor 100 (e.g., for storage in a non-volatile memory of the sensor 100, such as an EEPROM). In some embodiments, the transmitter 101 may convey the most recent filtered MSP value to the sensor 100 periodically (e.g., every 12 or 24 hours) and in case of sensor performance deficiency (see below). However, in some alternative embodiments, the filtered MSP values may be conveyed to the sensor 100 for storage in the sensor memory immediately regardless of the time. In some embodiments, the transmitter 100 may obtain previous MSP values from the memory of the sensor 100 in the event MSP values in the transmitter 101 (e.g., in an MSP buffer in the memory 922) are deleted (e.g., during a transmitter reset).

In some embodiments, calculating MSP may include calculating responsivity. In some embodiments, the transmitter 101 (e.g., the PIC microcontroller 920 of the transmitter 101) may determine whether to calculate responsivity at each calibration point. In some non-limiting embodiments, the transmitter 101 may calculate responsivity when there are at least a number of calibration points with a minimum range in the past time period. In some non-limiting embodiments, the minimum number of calibration points may be, for example and without limitation, 3. In some non-limiting embodiments, the minimum number of calibration points may be within a range from 2 to 14. In some non-limiting embodiments, the range may be, for example and without limitation, 50 mg/dL. In some non-limiting embodiments, the range may be within a range from 10 mg/dL to 100 mg/dL, and this range should be understood as describing and disclosing all range values (including all decimal or fractional minimum range values) and sub-ranges within this range. In some non-limiting embodiments, the past time period may be, for example and without limitation, 172,800 seconds. In some non-limiting embodiments, the past time period may be within a range from 1 hour to 1 month, and this range should be understood as describing and disclosing all past time period values (including all seconds) and sub-ranges within this range. In some non-limiting embodiments, calculating responsivity may include pairing the calibration points with their closest sensor measurement.

In some non-limiting embodiments, calculating responsivity may include correcting the SigOnOff_nA to 37C (termed as SigOnOff_sensor_37C) using a temperature correction term. In some non-limiting embodiments, the SigOnOff_nA may be the digitized output of the signal photodetector 224, which is sensitive to emission light 331 from the indicator molecules 104 of the analyte indicator element 106. In some non-limiting embodiments, the temperature correction term may be, for example and without limitation, 0.02. In some non-limiting embodiments, the temperature correction term may be within a range from 0-100%, and this range should be understood as describing and disclosing all temperature correction term values (including all decimal or fractional values) and sub-ranges within this range. In some non-limiting embodiments, calculating responsivity may include calculating the "supposed" SigOnOff_nA at manufacturing testing (termed as SigOnOff_QC) through the inverse kd equation. In some embodiments, the inverse kd equation is the G=kd*(s−smin)/(smax−s) equation flipped around to solve for s. In some embodiments, the responsivity may be defined as the ratio of the standard deviation of the two signals:

responsivity=std(SigOnOff_sensor_37C)/std(SigOnOff_QC).

In some non-limiting embodiments, if the calculated responsivity is greater than a threshold, the transmitter 101 may pass the responsivity through a curve fitting to make sure the final responsivity is less than or equal to 1. In some non-limiting embodiments, the threshold may be, for example and without limitation, 0.8. In some non-limiting embodiments, the threshold may be within a range from 0.60 to 0.99, and this threshold range should be understood as describing and disclosing all normalized signal values (including all decimal or fractional values) and sub-ranges within this range.

In some embodiments, calculating MSP may include calculating a signal normalize to its manufacturing values. In some embodiments, the transmitter 101 may calculate the normalized signal. In some embodiments, the normalized signal may be the ratio between the temperature corrected signal subtracted by the opacity and LED spillover at manufacturing testing and the baseline signal subtracted by the opacity and LED spillover at manufacturing testing. In some embodiments, the opacity and LED spillover may be offset/noise components convoluted in the total light arriving at the photodetector. In some embodiments, the normalized signal is defined as:

Normalized Signal =

$$\frac{SigOnOff_{nA} * (1 + Cth * (\text{Temperature} - 37)) - Zgel - Zbleed}{Sig0 - Zgel - Zbleed},$$

where SigOnOffnA is the signal in nano-amps, Cth is the temperature correction term, Sig0 is the baseline signal from manufacturing testing, Zgel is the opacity at manufacturing testing, and Zbleed is the LED spillover at manufacturing testing. In some embodiments, if the calculated normalized signal is greater than a threshold, the transmitter 101 may pass the normalized signal through a curve fitting to make sure the final normalized signal is less than or equal to 1. In some non-limiting embodiments, the threshold may be, for example and without limitation, 0.8. In some non-limiting embodiments, the threshold may be within a range from 0.60 to 0.99, and this threshold range should be understood as describing and disclosing all normalized signal values (including all decimal or fractional values) and sub-ranges within this range. For example, in some non-limiting embodiments, the final normalized signal may be equal to 1−MSP_alpha*exp(−normalized signal/MSP_tau). In some non-limiting embodiments, MSP_alpha and MSP_tau may be equal to, for example and without limitation, 10.9196 and 0.2, respectively. However, this is not required, and, in some alternative embodiments, the transmitter 101 may use different values for one or more of MSP_alpha and MSP_tau.

Figure 6:
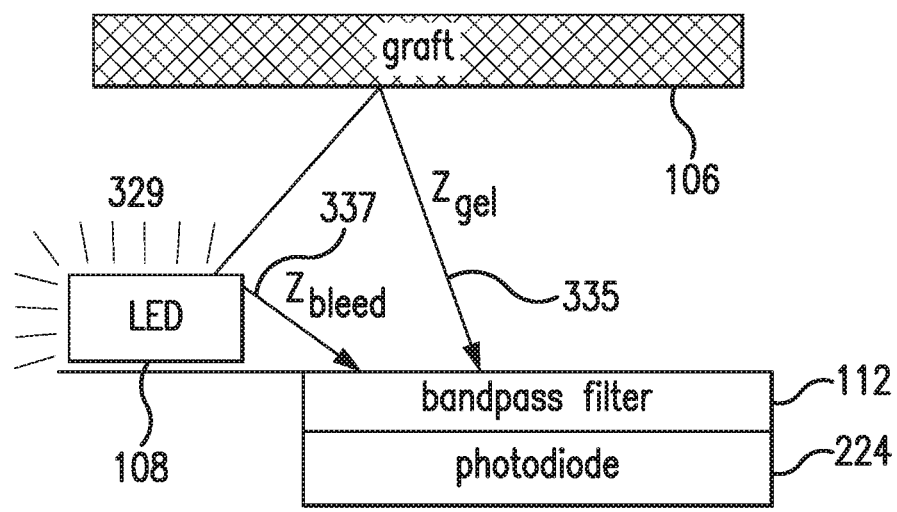
FIG. 6 illustrates the components of the excitation light received by the photodetector that contribute to the offset in the raw signal in accordance with an embodiment of the present invention.
Figure 7C:
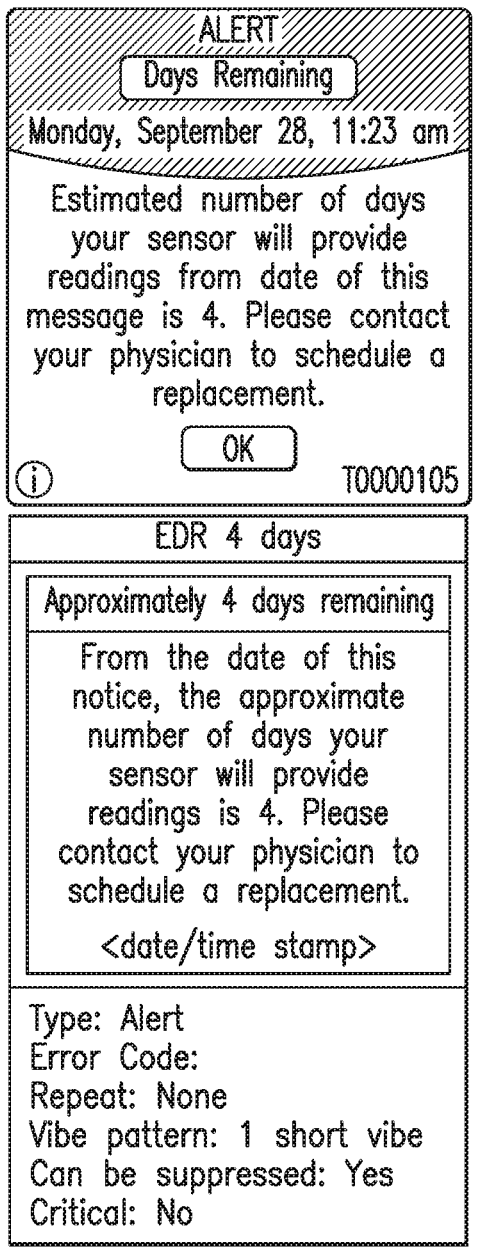
Figure 7D:
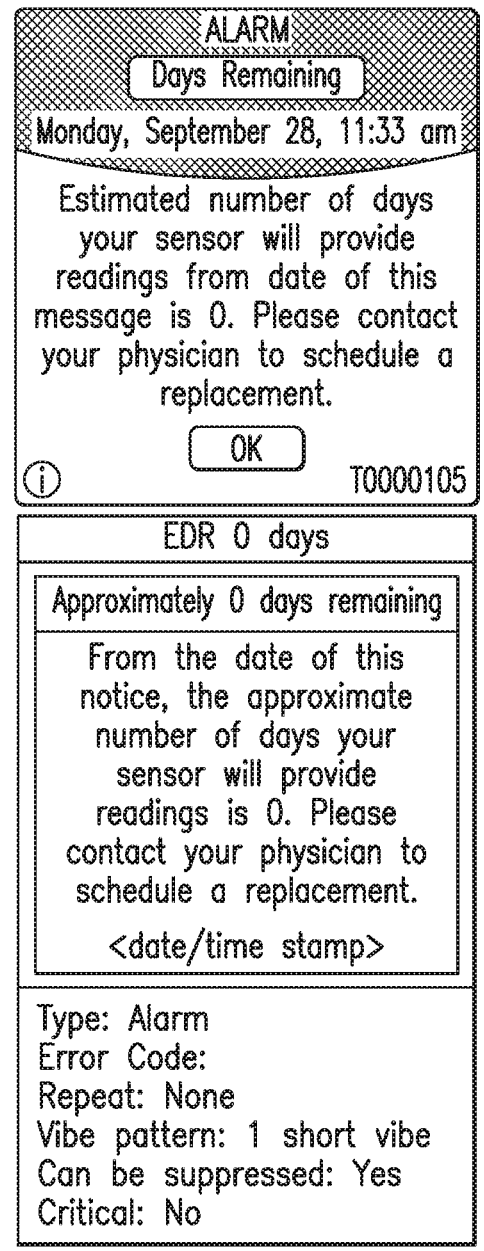

FIG. 6 illustrates the Zgel (i.e., opacity) and Zbleed offset components that may be in the light that reaches a photodetector of the sensor 100. As illustrated in FIG. 6, the excitation light 329 emitted from light source 108 that reaches the photodetector may include (i) a reflection light component 335 that is reflected from the analyte indicator element 106 (e.g., indicator molecules 104 in a gel) before reaching the photodetector and (ii) a bleed light component 337 that reaches the photodetector without encountering the analyte indicator element 106. The reflection light component 335 may produce a reflection component $Z_{gel}$ of the offset, and the bleed light component 337 may produce a bleed component $Z_{bleed}$ of the offset Z.

In some embodiments, the Zgel and Zbleed offset components may be measured during the manufacturing of the sensor 100 (i.e., at manufacturing testing). As noted above, in some embodiments, the transmitter 101 may use the Zgel and Zbleed offset components measured at manufacturing testing to calculate the normalized signal. However, the Zgel offset component may increase due to photobleaching of the indicator molecules 104. In particular, as indicator molecules 104 become photo-bleached, the overall absorbance of the analyte indicator element 106 decreases, which increases the reflectance of the analyte indicator element 106, the amount of excitation light 329 reflected from the analyte indicator element 106, and the intensity of the reflection light component 335. Accordingly, in some alternative embodiments, in order to compensate for the increasing Zgel offset component in the raw signal, the transmitter 101 may dynamically track the Zgel offset component and use the dynamically tracked Zgel offset component to calculate the normalized signal.

In some embodiments, the embodiments, the transmitter 101 may dynamically track the Zgel offset component by tracking the cumulative photo bleaching time $t_{pb}$ (e.g., by tracking the cumulative emission time $t_e$ of the light source 108), and the dynamically tracked Zgel offset component may be defined as:

$$Z_{gel}(t_{pb}) = Z_{gel}(1 + \phi_Z(1 - e^{-k_{pb}t_{pb}}))$$

where $Z_{gel}(t_{pb})$ is the dynamically tracked Zgel offset component, $t_{pb}$ is the cumulative photo bleaching time, $\phi_z$ is the percent increase of $Z_{gel}$ when the indicator is fully photo-bleached, and $k_{pb}$ is the rate of photobleaching. In some alternative embodiments where the transmitter 101 uses the dynamically tracked Zgel offset component to calculate the normalized signal, the normalized signal may be the ratio between the temperature corrected signal (i.e., SigOnOffnA*(1+Cth*(Temperature−37))) subtracted by the dynamically tracked opacity (i.e., $Z_{gel}(t_{pb})$) and the LED spillover at manufacturing testing (i.e., Zbleed) and the baseline signal (i.e., Sig0) subtracted by the opacity and LED spillover at manufacturing testing (i.e., Zgel and Zbleed, respectively).

In some embodiments, calculating MSP may include calculating normMARD. In some embodiments, the transmitter 101 may calculate normMARD. MARD stands for mean absolute relative deviation. In some embodiments, normMARD may be defined as the absolute value of difference between the sensor measurement (e.g., the measurement generated by the signal photodetector 224, which may be indicative of the level of emission light 331 from the indicator molecules 104 of the analyte indicator element 106) and the reference measurement (e.g., the measurement generated by the reference photodetector 226, which may be indicative of the level of reflection light 333) divided by the reference measurement. In other words, in some embodiments, normMARD may be defined as the absolute value of the difference between the sensor measurement and the reference measurement divided by the reference measurement. In other words, in some embodiments:

normMARD=$|M_S-M_R|/M_R$, where $M_S$ is the sensor measurement, and $M_R$ is the reference measurement.

In some non-limiting embodiments, calculation of normMARD by the transmitter 101 may include calculating MARD using the most recent calibration point and calculated analyte concentration pairs in a period of time (e.g., the calibration point and sensor measurement pairs in the past 2 days). In some embodiments, the transmitter 101 may use the latest sensor measurements within the past 5 minutes of the calibration point for the MARD calculation. In some embodiments, after calculating MARD, the transmitter 101 may calculate normMARD using the calculated MARD. In some non-limiting embodiments, the transmitter 101 may calculate normMARD using the calculated MARD as follows:

normMARD=$p0*(p1+\text{erf}((p2-\text{MARD})/p3))$, where erf(x) is the error function. In this way, the lower the normMARD is, the worse the sensor performance is. In some non-limiting embodiments, p0, p1, p2, and p3 may be 0.5, 1, 100, and 0.2, respectively. However, this is not required, and, in some alternative embodiments, the transmitter 101 may use different parameters to calculate normMARD.

In some embodiments, calculating MSP may include calculating normLc. In some embodiments, the transmitter 101 may calculate normLc. Lc represents fibrous capsule length (e.g., the distance between the analyte sensor 100 and a capillary of the body in which the sensor 100 is implanted). In some embodiments, the transmitter 101 may calculate Lc (e.g., from calibration point and sensor measurement pairs). However, this is not required, and, in some alternative embodiments, the transmitter 101 may use a default value for Lc. In some embodiments, the transmitter 101 may calculate normLc using the Lc. In some non-limiting embodiments, the transmitter 101 may calculate normLc using the Lc as follows:

norm$Lc=p4*(p5+\text{erf}((p6-Lc)/p7))$, where erf(x) is the error function. In this way, the lower the normLc is, the worse the sensor performance is. In some non-limiting embodiments, p4, p5, p6, and p7 may be 0.5, 1, 100, and 100, respectively. However, this is not required, and, in some alternative embodiments, the transmitter 101 may use different parameters to calculate normLc.

In some embodiments, after calculating MSP, the analyte monitoring system 50 may use the calculated MSP determine whether performance of the analyte sensor 100 is unsuitable for continuous analyte monitoring. In some embodiments, the transmitter 101 of the analyte monitoring system 50 may determine whether sensor performance is unsuitable for continuous analyte monitoring. In some embodiments, the transmitter 101 will determine that the performance of the analyte sensor 100 is deficient if MSP is below an MSP deficiency threshold. In some non-limiting embodiments, the MSP deficiency threshold may be, for example and without limitation, 0.35. In some non-limiting embodiments, the MSP deficiency threshold may be within a range from 1 to zero, and this MSP range should be understood as describing and disclosing all MSP values (including all decimal or fractional MSP values) and subranges within this range. In some embodiments, the transmitter 101 will determine that the performance of the analyte sensor 100 is deficient if MSP is below the MSP deficiency threshold for at least a period of time. In some non-limiting embodiments, the period of time may be, for example and without limitation, 3600 seconds. In some non-limiting embodiments, the period of time may be within a range from one second to 10 days, and this period of time range should be understood as describing and disclosing all periods of time (including all decimal or fractional seconds) and subranges within this range. In some embodiments, the transmitter 101 will only determine that the performance of the analyte sensor 100 is deficient if (i) MSP is below the MSP deficiency threshold for at least the period of time and (ii) an initialization period (e.g., a period of, for example and without limitation, 864,000 seconds, which may represent the maximum time the analyte sensor 100 would require for hydration after implantation) has passed since the analyte sensor 100 was implanted. In some non-limiting embodiments, the transmitter 101 may approximate the sensor implant time as the time at which the transmitter 101 is paired with the analyte sensor 100, which typically occurs immediately after implant.

In some embodiments, the MSP values for each of the sensors start at 1. In some non-limiting embodiments, the performance of the sensors is determined to be deficient when the MSP goes below an MSP deficiency threshold of 0.35, and, for each sensor, the corresponding transmitter stops conveying analyte concentration information (e.g., to a display device for display) when the transmitter determines the sensor performance to be deficient.

In some embodiments, if the transmitter 101 determines that the performance of the analyte sensor 100 is deficient, the analyte monitoring system 50 may consider the sensor 100 to no longer be suitable for continuous analyte monitoring, and the transmitter 101 may trigger a sensor retirement alarm, which the transmitter 101 may convey to the display device 105.

In some embodiments, the analyte monitoring system 50 may perform sensor delamination detection. In some non-limiting embodiments, sensor delamination may result in a signal having a rate of change over a predefined threshold. That is, sensor delamination may result in a sudden jump in the signal, either a jump up or a jump down. In some embodiments, a sensor delamination detection algorithm may be used to prevent erroneous sensor measurement output when delamination occurs and/or to trigger a sensor instability alarm. In some embodiments, circuitry of the transmitter 101 (e.g., the PIC microcontroller 920) may perform the sensor delamination detection. In some embodiments, the transmitter 101 may detect sensor delamination when SigOnOff_nA changes drastically for a number of consecutive sensor measurements (e.g., two consecutive sensor measurements). In some non-limiting embodiments, the transmitter 101 may determine that SigOnOff_nA has changed drastically for consecutive sensor measurements if consecutive sensor measurements, which are at least a time period apart, have a rate of change in SigOnOff_nA that is greater than a rate of change threshold (e.g., 0.1 na/second). In some non-limiting embodiments, the sensor measurements may be, for example and without limitation, measurements generated by the signal photodetector 224, which may be indicative of the level of emission light 331 from the indicator molecules 104 of the analyte indicator element 106. In some non-limiting embodiments, the time period apart may be, for example and without limitation, 100 seconds apart. In some non-limiting embodiments, the time period may be within a range from 0 seconds to 300 seconds, and this time period range should be understood as describing and disclosing all seconds and sub-ranges within this range. In some non-limiting embodiments, the rate of change threshold may be, for example and without limitation, 0.1 na/second. In some non-limiting embodiments, the rate of change threshold may be within a range from 0.01 na/second to 1.0 na/second, and this rate of change threshold range should be understood as describing and disclosing all rates of change and sub-ranges within this range.

In some embodiments, the transmitter 101 additionally or alternatively performs sensor delamination detection based on reference measurements. In some non-limiting embodiments, the reference measurements may be, for example and without limitation, generated by the reference photodetector 226, which may be indicative of the level of reflection light 333. In some embodiments, when the transmitter 101 detects sensor delamination, the transmitter 101 may trigger a sensor instability alarm.

In some non-limiting embodiments, in response to a sensor instability alarm, the transmitter 101 may do one or more of the following: (i) convey the sensor instability alarm to the display device 105, (ii) blind the sensor output (i.e., stop conveying calculated analyte concentrations to the display device 105 for display), and (iii) return to the initialization phase. In some embodiments, the initialization phase may be, for example and without limitation, a calibration phase after sensor insertion. In some embodiments, calibrations are entered more frequently during the initialization than during normal operation (e.g., 4 calibrations per day instead of 2 calibrations per day).

In some embodiments, the analyte monitoring system 50 may predict the end of the functional life of an implanted analyte sensor 100. The manner in which a body (e.g., a human body) responds to an analyte sensor 100 implanted (fully or partially) in the body may vary widely from body to body. That is, the body's response to an implanted analyte sensor 100 may vary on a patient by patient basis. Accordingly, in some embodiments, the analyte monitoring system 50 may utilize information on the performance of the analyte sensor 100 and/or the body's response to the analyte sensor 100 in order to predict the end of the functional life of analyte sensor 100.

In some embodiments, the transmitter 101 of the analyte monitoring system 50 may predict the end of the functional life of the implanted analyte sensor 100. In other words, in some embodiments, the transmitter 101 may predict the number the number of days remaining before the sensor performance is determined to be deficient for use in continuous analyte monitoring. In some embodiments, the transmitter 101 may use the assessment of sensor performance, which may be based on the metric for real time assessment of sensor performance (MSP), to predict the sensor end of life (EOL). In some embodiments, the transmitter 101 may use time since the sensor 100 was implanted (in addition to or as an alternative to the assessment of sensor performance) to predict the sensor EOL.

In some embodiments, the transmitter 101 may associate one or more sensor performance assessment thresholds and/or one or more time since implant thresholds with one or more predictions of time remaining before sensor EOL. In some embodiments, if the transmitter 101 calculates an MSP value less than a sensor performance assessment threshold or if the time since implant exceeds a time since implant threshold, the transmitter 101 may predict the associated amount of time remaining before sensor EOL. In some embodiments, the transmitter 101 may convey the predicted amount of time remaining before sensor EOL to the display device 105 (e.g., as a notification, alert, or alarm), and the display device 105 may display an appropriate indication of the predicted amount of time remaining before sensor EOL. FIGS. 7A-7D illustrate non-limiting examples of indications of the predicted amount of time remaining before sensor EOL, which may be displayed by the display device 105 in accordance with some non-limiting embodiments.

For example, in some non-limiting embodiments, the transmitter 101 may associate a first performance threshold and/or a first time since implant threshold (e.g., 136 days) with a first amount of time (e.g., 14 days for a 150 day lifetime device) remaining before sensor EOL. In some non-limiting embodiments, the first performance threshold may be, for example and without limitation, 0.47. In some non-limiting embodiments, the first performance threshold may be within a range from 1 to 0.05, and this first performance threshold range should be understood as describing and disclosing all thresholds (including all decimal or fractional threshold values) and sub-ranges within this range. In some non-limiting embodiments, the first time since implant threshold may be, for example and without limitation, 136 days since implant for a 150 day lifetime device. In some non-limiting embodiments, the first time since implant threshold may be within a range from 5 to 730 days, and this first time since implant threshold range should be understood as describing and disclosing all times (including all seconds) and sub-ranges within this range. In some non-limiting embodiments, the first amount of time may be, for example and without limitation, 14 days. In some non-limiting embodiments, the first amount of time may be within a range from 50 to 3 days, and this first amount of time range should be understood as describing and disclosing all times (including all seconds) and sub-ranges within this range.

In some embodiments, if the transmitter 101 calculates an MSP value less than the first performance threshold or if the time since implant exceeds the first time since implant threshold, the transmitter 101 may predict the first amount of time remaining before sensor EOL. In some embodiments, the transmitter 101 may convey the prediction of the first amount of time remaining before sensor EOL to the display device 105 (e.g., as a notification, alert, or alarm), and the display device 105 may display an appropriate indication of the prediction of the first amount of time remaining before sensor EOL. See, for example and without limitation, FIG. 7B.

In some non-limiting embodiments, the transmitter 101 may additionally or alternatively associate one or more finer grain performance thresholds, such as, for example and without limitation, a second performance threshold and/or a second time since implant threshold with a second amount of time remaining before sensor EOL. In some non-limiting embodiments, the second performance threshold may be, for example and without limitation, 0.38. In some non-limiting embodiments, the second performance threshold may be within a range from 1 to 0.05, and this second performance threshold range should be understood as describing and disclosing all thresholds (including all decimal or fractional threshold values) and sub-ranges within this range. In some non-limiting embodiments, the second time since implant threshold may be, for example and without limitation, 146 days since implant. In some non-limiting embodiments, the second time since implant threshold may be within a range from 5 to 730 days, and this second time since implant threshold range should be understood as describing and disclosing all times (including all seconds) and sub-ranges within this range. In some non-limiting embodiments, the second amount of time may be, for example and without limitation, 4 days. In some non-limiting embodiments, the second amount of time may be within a range from 30 days to 1 day, and this second amount of time range should be understood as describing and disclosing all times (including all seconds) and sub-ranges within this range.

In some embodiments, if the transmitter 101 calculates an MSP value less than the second performance threshold or if the time since implant exceeds the second time since implant threshold, the transmitter 101 may predict the second amount of time remaining before sensor EOL. In some embodiments, the transmitter 101 may convey the prediction of the second amount of time remaining before sensor EOL to the display device 105 (e.g., as a notification, alert, or alarm), and the display device 105 may display an appropriate indication of the prediction of the second amount of time remaining before sensor EOL. See, for example and without limitation, FIG. 7C.

In some non-limiting embodiments, the transmitter 101 may additionally or alternatively associate a third performance threshold (e.g., 0.36) and/or a third time since implant threshold (e.g., 150 days since implant) with a third amount of time remaining before sensor EOL (e.g., 0 days). In some non-limiting embodiments, the third performance threshold may be, for example and without limitation, 0.36. In some non-limiting embodiments, the third performance threshold may be within a range from 1 to 0.05, and this third performance threshold range should be understood as describing and disclosing all thresholds (including all decimal or fractional threshold values) and sub-ranges within this range. In some non-limiting embodiments, the third time since implant threshold may be, for example and without limitation, 150 days since implant for a 150 day device. In some non-limiting embodiments, the third time since implant threshold may be within a range from 7 to 730 days, and this third time since implant threshold range should be understood as describing and disclosing all times (including all seconds) and sub-ranges within this range. In some non-limiting embodiments, the third amount of time may be, for example and without limitation, 0 days. In some non-limiting embodiments, the third amount of time may be within a range from 20 to 0 days, and this third amount of time range should be understood as describing and disclosing all times (including all seconds) and sub-ranges within this range.

In some embodiments, if the transmitter 101 calculates an MSP value less than the third performance threshold or if the time since implant exceeds the third time since implant threshold, the transmitter 101 may predict the third amount of time remaining before sensor EOL. In some embodiments, the transmitter 101 may convey the prediction of the third amount of time remaining before sensor EOL to the display device 105 (e.g., as a notification, alert, or alarm), and the display device 105 may display an appropriate indication of the prediction of the third amount of time remaining before sensor EOL. See, for example and without limitation, FIG. 7D.

In some non-limiting embodiments, the transmitter 101 may additionally or alternatively associate one or more other performance thresholds and/or one or more other times since implant threshold with one or more other amounts of time remaining before sensor. In some embodiments, if the transmitter 101 calculates an MSP value less than another performance thresholds or if the time since implant exceeds another time since implant threshold, the transmitter 101 may predict another amount of time remaining before sensor EOL. In some embodiments, the transmitter 101 may convey a prediction of another amount of time remaining before sensor EOL to the display device 105 (e.g., as a notification, alert, or alarm), and the display device 105 may display an appropriate indication of the prediction of the other amount of time remaining before sensor EOL. See, for example and without limitation, FIG. 7A.

In some embodiments, the analyte monitoring system 50 may use different colors to distinguish between levels of severity with respect to how close the sensor is to the predicted end of life. For example, in some non-limiting embodiments, the analyte monitoring system 50 may use blue, yellow, and red on the display device 105 to distinguish between low, intermediate, and high levels of severity, respectively (e.g., blue may be used for the displays shown in FIGS. 7A and 7B, yellow may be used for the displays shown in FIG. 7C, and red may be used for displays shown in FIG. 7D). However, this is not required, and some alternative embodiments may use different colors and/or different numbers of colors to indicate to distinguish between levels of severity with respect to how close the sensor is to the predicted end of life.

Figure 8:
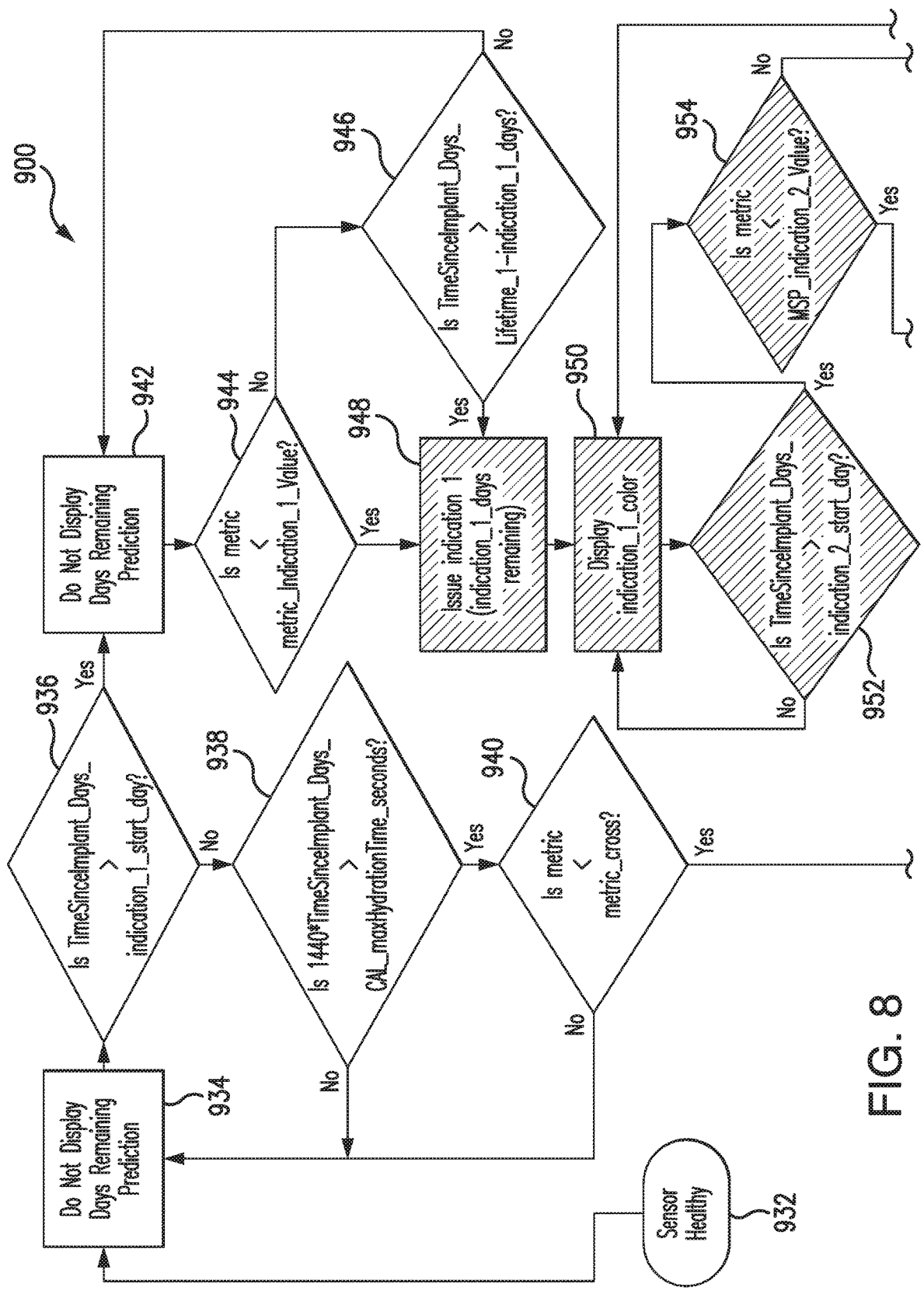
FIG. 8 is a flow chart illustrating a process for predicting sensor EOL embodying aspects of the present invention.
Figure 9A:
Figure 9B:
Figure 10:
Figure 11:
Figure 12:
Figure 13:
Figure 17:
Figure 19:
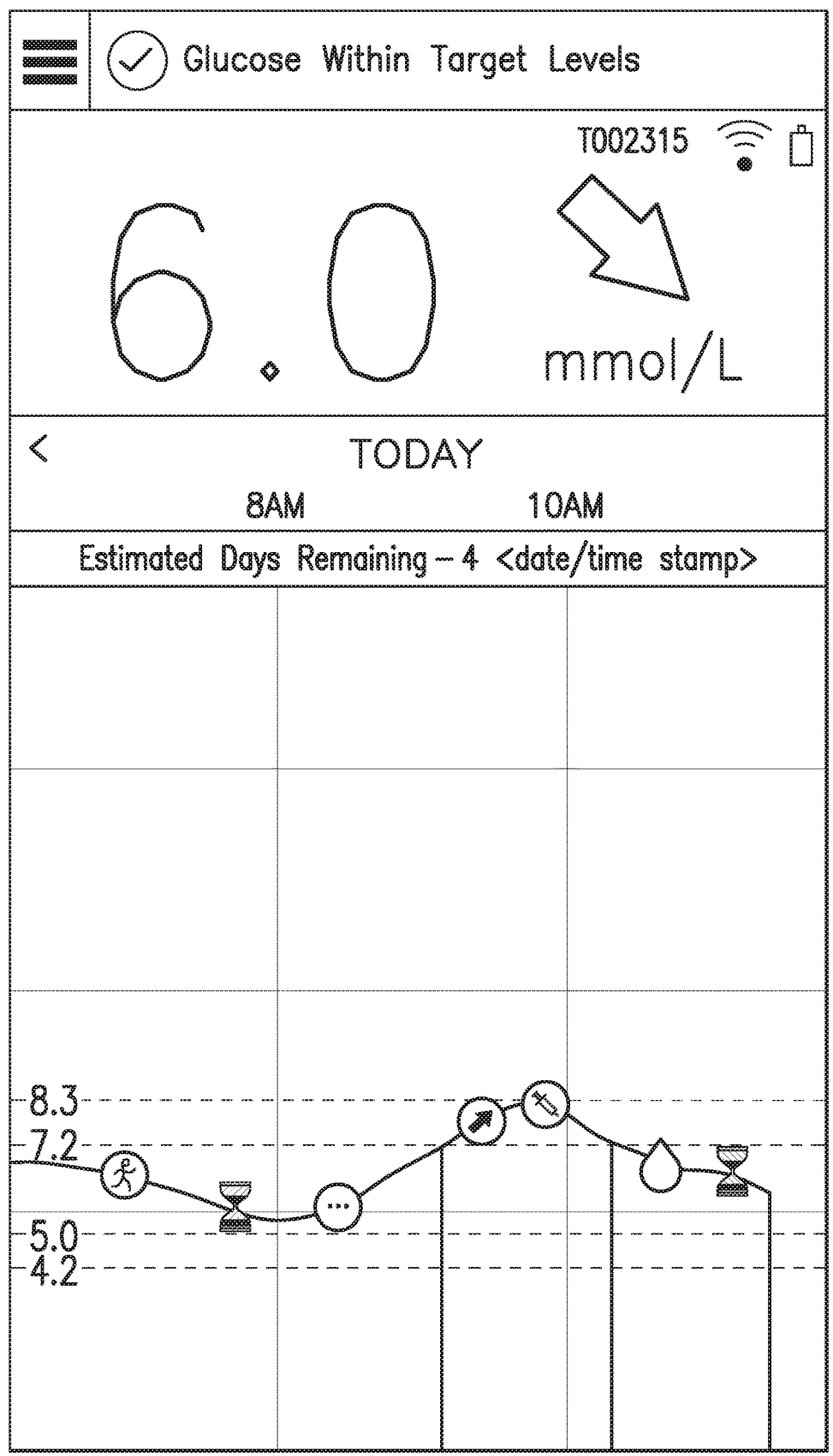
Figure 21:
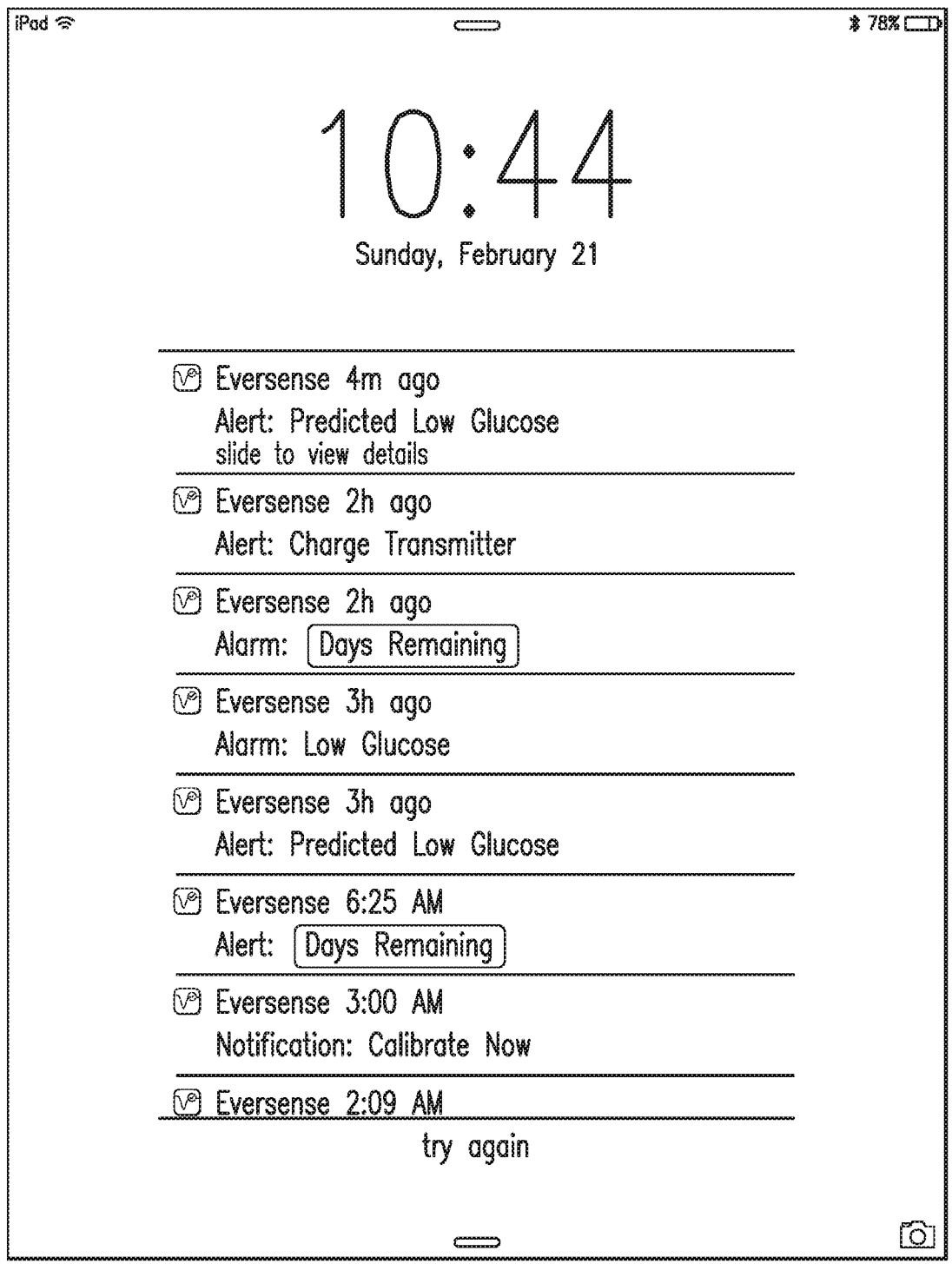

FIG. 8 is a flow chart illustrating a process 900 for predicting sensor EOL according to some embodiments. In some embodiments, the transmitter 101 performs one or more steps of the sensor EOL prediction process 900. In some embodiments, the transmitter 101 issues indications of the prediction(s) to the display device 105. In some embodiments, the process 900 may begin in step 932 with a healthy sensor 100 implanted in the body of a living animal. In some non-limiting embodiments, the healthy sensor 100 may have a sensor performance assessment value (e.g., an MSP value) at or near 1. In some embodiments, the process 900 may include a step 934 in which the transmitter 101 does not convey predictions of time (e.g., days) remaining before sensor EOL to the display device 105, and the display device 105 does not display a sensor EOL prediction. In some non-limiting embodiments, in step 934, the transmitter 101 may convey an indication of time (e.g., days) since implant to the display device 105, and the display device 105 may display an indication of time (e.g., days) since implant. See, for example, FIG. 9B.

In some embodiments, the process 900 may include a step 936 in which the transmitter 101 compares the time since implant to an initial prediction indication threshold. In some embodiments, the initial prediction indication threshold may be, for example and without limitation, 76 days since implant. In some non-limiting embodiments, the initial prediction indication threshold may be within a range from 5 to 150 days, and this initial prediction indication threshold range should be understood as describing and disclosing all times (including all seconds) and sub-ranges within this range. If the time since implant is greater than the initial prediction indication threshold, the process 900 may proceed to a step 942. However, if the time since implant is not greater than the initial prediction indication threshold, the process 900 may proceed to a step 938.

In some embodiments, the process 900 may include a step 938 in which the transmitter 101 compares the time since implant to a maximum hydration time, which may correspond to maximum time the analyte sensor 100 would require for hydration after implantation. In some embodiments, the maximum hydration time may be, for example and without limitation, 10 days). In some non-limiting embodiments, the maximum hydration time may be within a range from 0 to 30 days, and this maximum hydration time range should be understood as describing and disclosing all times (including all seconds) and sub-ranges within this range. If the time since implant is greater than maximum hydration time, the process 900 may proceed to a step 940. However, if the time since implant is not greater than the maximum hydration time, the process 900 may proceed back to step 934.

In some embodiments, the process 900 may include a step 940 in which the transmitter 101 compares an assessment of sensor performance (e.g., MSP) to a deficiency threshold (e.g., 0.35), which may correspond the sensor performance at which the sensor becomes unsuitable for the continuous analyte monitoring. If the comparison of the assessment of sensor performance to the deficiency threshold indicates that the sensor performance is deficient (e.g., if the assessment of sensor performance is less than the deficiency threshold for at least a period of time such as, for example, 3600 seconds), the process 900 may proceed to a step 974 in which the sensor is retired. However, if the comparison in step 940 does not indicate that the sensor performance is deficient, the process 900 may proceed back to step 934. In some embodiments, because step 940 is not performed until after the sensor 100 has had sufficient time for hydration after implantation, the process 900 may avoid premature sensor retirement due to poor sensor performance caused by incomplete hydration.

In some embodiments, the process 900 may include a step 942 in which the transmitter 101 does not convey predictions of time (e.g., days) remaining before sensor EOL to the display device 105, and the display device 105 does not display a sensor EOL prediction. In some non-limiting embodiments, in step 942, the transmitter 101 may convey an indication of time (e.g., days) since implant to the display device 105, and the display device 105 may display an indication of time (e.g., days) since implant. See, for example, FIG. 9B.

In some embodiments, the process 900 may include a step 944 in which the transmitter 101 compares an assessment of sensor performance (e.g., MSP) to a first performance threshold (e.g., 0.47). If the assessment of sensor performance is less than the first performance threshold, the process 900 may proceed to a step 948. However, if the assessment of sensor performance is not less than the first performance threshold, the process 900 may proceed to a step 946.

In some embodiments, the process 900 may include a step 946 in which the transmitter 101 compares the time since implant to a first time since implant threshold (e.g., 136 days since implant for a 150 day device). If the time since implant is greater than the first time since implant threshold, the process 900 may proceed to the step 948. However, if the time since implant is not greater than the first time since implant threshold, the process 900 may proceed back to step 942.

In some embodiments, the process 900 may include a step 948 in which the transmitter 101 predicts a first amount of time (e.g., 14 days) remaining before sensor EOL. In some embodiments, in step 948, the transmitter 101 may convey the prediction of the first amount of time remaining before sensor EOL to the display device 105 (e.g., as a notification, alert, or alarm).

In some embodiments, the process 900 may include a step 950 in which the display device 105 displays an appropriate indication of the prediction of the first amount of time (e.g., 14 days) remaining before sensor EOL. In some embodiments, the display device 105 may use a first color (e.g., blue) to indicate a low level of severity with respect to how close the sensor is to the predicted end of life. See, for example and without limitation, FIG. 7B.

In some embodiments, the process 900 may include a step 952 in which the transmitter 101 compares the time since implant to a second prediction indication threshold (e.g., 77 days). If the time since implant is greater than the second prediction indication threshold, the process 900 may proceed to a step 954. However, if the time since implant is not greater than the second prediction indication threshold, the process 900 may proceed to back to step 950. In some alternative embodiments, the process 900 may not include a step 952, and the process 900 may proceed from step 950 directly to step 954.

In some embodiments, the process 900 may include a step 954 in which the transmitter 101 compares an assessment of sensor performance (e.g., MSP) to a second performance threshold (e.g., 0.38). If the assessment of sensor performance is less than the second performance threshold, the process 900 may proceed to a step 958. However, if the assessment of sensor performance is not less than the second performance threshold, the process 900 may proceed to a step 956.

In some embodiments, the process 900 may include a step 956 in which the transmitter 101 compares the time since implant to a second time since implant threshold (e.g., 146 days since implant). If the time since implant is greater than the second time since implant threshold, the process 900 may proceed to the step 958. However, if the time since implant is not greater than the second time since implant threshold, the process 900 may proceed back to step 950.

In some embodiments, the process 900 may include a step 958 in which the transmitter 101 predicts a second amount of time (e.g., 4 days) remaining before sensor EOL. In some embodiments, in step 958, the transmitter 101 may convey the prediction of the second amount of time remaining before sensor EOL to the display device 105 (e.g., as a notification, alert, or alarm).

In some embodiments, the process 900 may include a step 960 in which the display device 105 displays an appropriate indication of the prediction of the second amount of time (e.g., 4 days) remaining before sensor EOL. In some embodiments, the display device 105 may use a second color (e.g., yellow) to indicate an intermediate level of severity with respect to how close the sensor is to the predicted end of life. See, for example and without limitation, FIG. 7C.

In some embodiments, the process 900 may include a step 962 in which the transmitter 101 compares an assessment of sensor performance (e.g., MSP) to the deficiency threshold (e.g., 0.35), which may correspond the sensor performance at which the sensor becomes unsuitable for the continuous analyte monitoring. If the comparison of the assessment of sensor performance to the deficiency threshold indicates that the sensor performance is deficient (e.g., if the assessment of sensor performance is less than the deficiency threshold for at least a period of time such as, for example and without limitation, 3600 seconds), the process 900 may proceed to the step 974 in which the sensor is retired. However, if the comparison in step 962 does not indicate that the sensor performance is deficient, the process 900 may proceed to a step 964.

In some embodiments, the process 900 may include a step 964 in which the transmitter 101 compares the time since implant to a third time since implant threshold (e.g., 150 days since implant). If the time since implant is greater than the third time since implant threshold, the process 900 may proceed to the step 966. However, if the time since implant is not greater than the third time since implant threshold, the process 900 may proceed back to step 960.

In some embodiments, the process 900 may include a step 966 in which the transmitter 101 predicts a third amount of time (e.g., 0 days) remaining before sensor EOL. In some embodiments, in step 966, the transmitter 101 may convey the prediction of the third amount of time remaining before sensor EOL to the display device 105 (e.g., as a notification, alert, or alarm).

In some embodiments, the process 900 may include a step 968 in which the display device 105 displays an appropriate indication of the prediction of the third amount of time (e.g., 0 days) remaining before sensor EOL. In some embodiments, the display device 105 may use a third color (e.g., red) to indicate a high level of severity with respect to how close the sensor is to the predicted end of life. See, for example and without limitation, FIG. 7D.

In some embodiments, the process 900 may include a step 970 in which the transmitter 101 compares an assessment of sensor performance (e.g., MSP) to the deficiency threshold (e.g., 0.35). If the comparison of the assessment of sensor performance to the deficiency threshold indicates that the sensor performance is deficient (e.g., if the assessment of sensor performance is less than the deficiency threshold for at least a period of time such as, for example and without limitation, 3600 seconds), the process 900 may proceed to the step 974 in which the sensor is retired. However, if the comparison in step 970 does not indicate that the sensor performance is deficient, the process 900 may proceed to a step 972.

In some embodiments, the process 900 may include a step 972 in which the transmitter 101 compares the time since implant to a fourth time since implant threshold. In some non-limiting embodiments, the fourth time since implant threshold may be, for example and without limitation, 153 days since implant. In some non-limiting embodiments, the maximum hydration time fourth time since implant threshold may be within a range from 50 to 733 days, and this fourth time since implant threshold range should be understood as describing and disclosing all times (including all seconds) and sub-ranges within this range. If the time since implant is greater than the fourth time since implant threshold, the process 900 may proceed to the step 974, where the sensor is retired. However, if the time since implant is not greater than the fourth time since implant threshold, the process 900 may proceed back to step 968. In some alternative embodiments, the process 900 may not include the step 972, and the process 900 may proceed from step 970 directly to step 968 if the comparison in step 970 does not indicate that the sensor performance is deficient.

In some embodiments, the process 900 may include a step 974 in which the transmitter 101 may issue a sensor retirement alarm. In some non-limiting embodiments, in response to a sensor retirement alarm, the transmitter 101 may do one or more of the following: (i) convey the sensor retirement alarm to the display device 105 and (ii) blind the sensor output (i.e., stop conveying calculated analyte concentrations to the display device 105 for display). In some embodiments, in response to receiving the sensor retirement alarm, the display device 105 may display an indication that the sensor needs to be replaced and/or that analyte concentrations will not be displayed until the after the sensor is replaced.

FIGS. 9-21 illustrate non-limiting examples of ways in which indications of the predicted amount of time remaining before sensor EOL (or time since implant) may be displayed by the display device 105 in accordance with some non-limiting embodiments.

In some embodiments, the transmitter 101 may use one or more previous MSP values to train an autoregressive (AR) model. In some non-limiting embodiments, the transmitter 101 may begin using MSP values to train the AR model after a period of time (e.g., 20 days) has passed since sensor implant. As noted above, in some non-limiting embodiments, the transmitter 101 may approximate the sensor implant time as the time at which the transmitter 101 is paired with the analyte sensor 100, which typically occurs immediately after implant. In some embodiments, the transmitter 101 may use the AR model to predict one or more future MSP values. If, within a prediction time period (e.g., one, two, three, or four weeks), the predicted MSP values cross an MSP deficiency threshold (e.g., 0.35) at which sensor performance is determined to be deficient (e.g., unsuitable for the continuous analyte monitoring), the transmitter 101 may use the time (e.g., day or hour) at which the predicted MSP crosses the MSP deficiency threshold as the predicted time of sensor EOL.

In some embodiments, the transmitter 101 may begin predicting the sensor EOL after a particular time has passed since the sensor 100 was implanted (e.g., 60 days since implant). In some embodiments, the transmitter 101 may predict sensor EOL periodically (e.g., after each calibration, daily, or every other day). In some embodiments, the frequency at which sensor EOL is predicted may vary over time (e.g., the transmitter 101 may predict sensor EOL more frequently the closer the sensor gets to EOL). In some embodiments, each time the transmitter 101 predicts sensor EOL (or each time the predicted time of sensor EOL is different than the previous predicted time of sensor EOL), the transmitter 101 may convey the predicted time of sensor EOL to the display device 105 (e.g., as a notification, alert, or alarm), and the display device 105 may display an appropriate indication of the predicted time of sensor EOL.

In some embodiments, the analyte monitoring system 50 may use different colors to distinguish between levels of severity with respect to how close the sensor is to the predicted end of life. For example, in some non-limiting embodiments, the analyte monitoring system 50 may use blue, yellow, and red on the display device 105 to distinguish between low, intermediate, and high levels of severity, respectively. In some non-limiting embodiments, low, intermediate, and high levels of severity may correspond to, for example and without limitation, 10 or more days until predicted sensor EOL, 4-9 days until predicted sensor EOL, and fewer than 4 days until predicted sensor EOL, respectively. However, this is not required, and, some alternative embodiments may use one or more different colors and/or different level of severity ranges.

Figure 22:
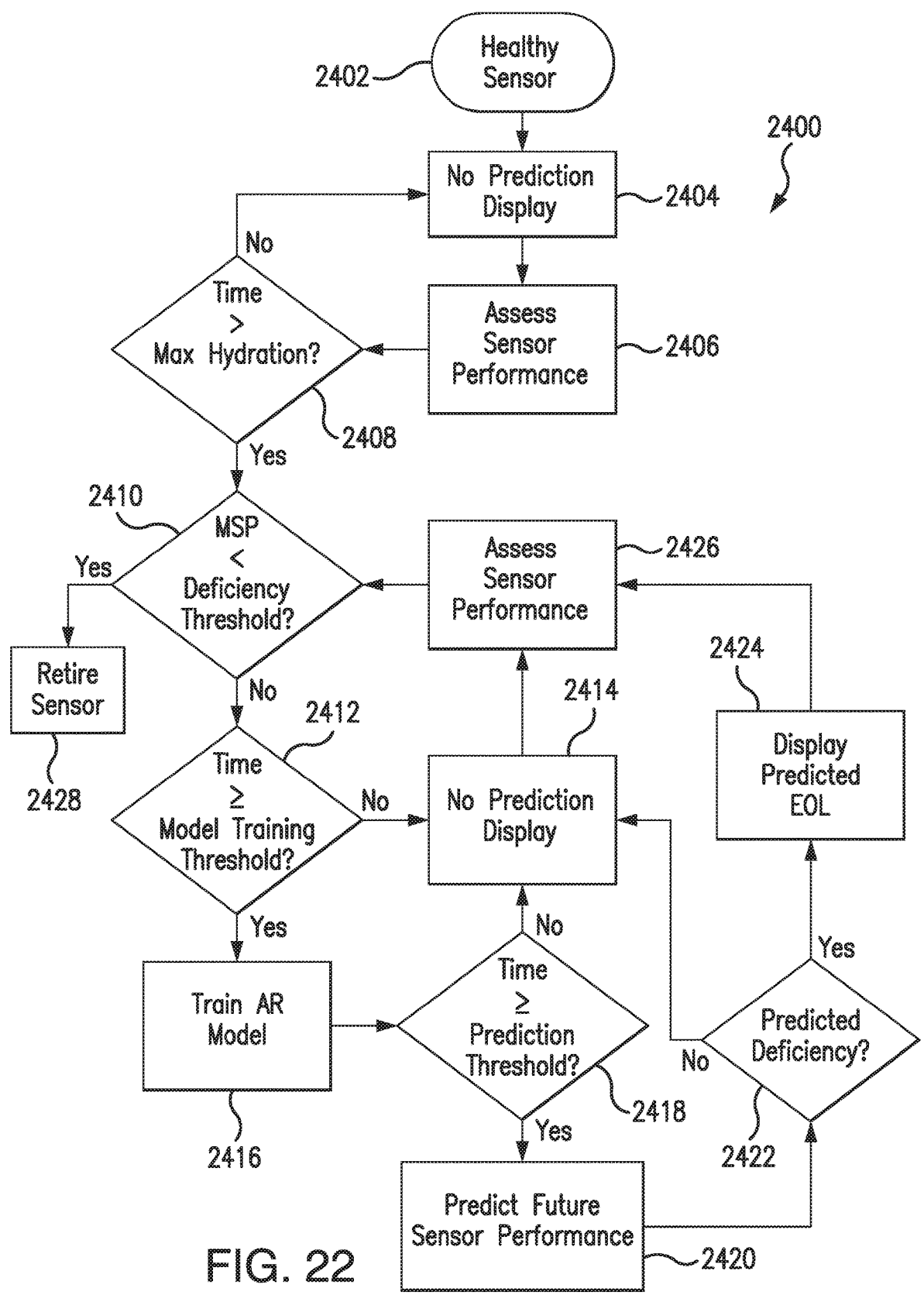
FIG. 22 is a flow chart illustrating a process for predicting sensor EOL embodying aspects of the present invention.

FIG. 22 is a flow chart illustrating a process 2400 for predicting sensor EOL according to some embodiments that use sensor performance assessments to train an AR model and use the AR model to predict future sensor performance assessments. In some embodiments, the transmitter 101 performs one or more steps of the sensor EOL prediction process 2400. In some embodiments, the process 2400 may begin in step 2402 with a healthy sensor 100 implanted in the body of a living animal. In some non-limiting embodiments, the healthy sensor 100 may have a sensor performance assessment value (e.g., an MSP value) at or near 1. In some embodiments, the process 2400 may include a step 2404 in which the transmitter 101 does not convey predictions of time (e.g., days) remaining before sensor EOL to the display device 105, and the display device 105 does not display a sensor EOL prediction. In some non-limiting embodiments, in step 2404, the transmitter 101 may convey an indication of time (e.g., days) since implant to the display device 105, and the display device 105 may display an indication of time (e.g., days) since implant.

In some embodiments, the process 2400 may include a step 2406 in which the transmitter 101 assesses the performance of the analyte sensor 100. In some non-limiting embodiments, the transmitter 101 may assess sensor performance by calculating an MSP for the sensor 100.

In some embodiments, the process 2400 may include a step 2408 in which the transmitter 101 compares the time since implant to a maximum hydration time (e.g., 10 days), which may correspond to maximum time the analyte sensor 100 would require for hydration after implantation. If the time since implant is greater than maximum hydration time, the process 2400 may proceed to a step 2410. However, if the time since implant is not greater than the maximum hydration time, the process 2400 may proceed back to step 2404.

In some embodiments, the process 2400 may include a step 2410 in which the transmitter 101 compares the assessment of sensor performance (e.g., the MSP value) to a deficiency threshold (e.g., 0.35), which may correspond the sensor performance at which the sensor becomes unsuitable for the continuous analyte monitoring. If the comparison of the assessment of sensor performance to the deficiency threshold indicates that the sensor performance is deficient (e.g., if the assessment of sensor performance is less than the deficiency threshold for at least a period of time such as, for example and without limitation, 3600 seconds), the process 2400 may proceed to a step 2428 in which the sensor is retired. However, if the comparison in step 2410 does not indicate that the sensor performance is deficient, the process 2400 may proceed to a step 2412. In some embodiments, because step 2410 is not performed until after the sensor 100 has had sufficient time hydrate after implantation, the process 2400 may avoid premature sensor retirement due to poor sensor performance caused by incomplete hydration.

In some embodiments, the process 2400 may include a step 2412 in which the transmitter 101 compares the time since implant to a model training threshold (e.g., 20 days). If the time since implant is greater than or equal to the model training threshold, the process 2400 may proceed to a step 2416 in which the sensor performance assessment is used to train a model. However, if the time since implant is not greater than the model training threshold, the process 2400 may proceed to a step 2414.

In some embodiments, the process 2400 may include a step 2414 in which the transmitter 101 does not convey predictions of time (e.g., days) remaining before sensor EOL to the display device 105, and the display device 105 does not display a sensor EOL prediction. In some non-limiting embodiments, in step 2414, the transmitter 101 may convey an indication of time (e.g., days) since implant to the display device 105, and the display device 105 may display an indication of time (e.g., days) since implant.

In some embodiments, the process 2400 may include a step 2416 in which the transmitter 101 uses the sensor performance assessment (e.g., the MSP value) calculated in step 2406 or step 2426 to train an autoregressive (AR) model.

In some embodiments, the process 2400 may include a step 2418 in which the transmitter 101 compares the time since implant to a prediction threshold (e.g., 60 days). If the time since implant is greater than or equal to the prediction threshold, the process 2400 may proceed to a step 2420 in which future sensor performance is predicted. However, if the time since implant is not greater than the model training threshold, the process 2400 may proceed to a step 2414.

In some embodiments, the process 2400 may include a step 2420 in which the transmitter 101 uses the AR model to predict future sensor performance. In some embodiments, in step 2420, the transmitter 101 may use the AR model to predict one or more future MSP values.

In some embodiments, the process 2400 may include a step 2422 in which the transmitter 101 determines whether the predicted future sensor performance crosses (i.e., falls below) the deficiency threshold (e.g., 0.35) within a prediction time period (e.g., one, two, three, or four weeks). If the predicted future sensor performance crosses the deficiency threshold within the prediction time period, the transmitter 101 may use the time (e.g., day or hour) at which the predicted sensor performance crosses the deficiency threshold as the predicted time of sensor EOL, and the process 2400 may proceed to a step 2424 in which the predicted time of sensor EOL is conveyed to the display device 105. However, if the predicted future sensor performance does not cross the deficiency threshold within the prediction time period, the process 2400 may proceed to the step 2414 in which no prediction of sensor EOL is conveyed to the display device 105.

In some embodiments, the process 2400 may include a step 2424 in which the transmitter 101 conveys a prediction of the amount of time remaining before sensor EOL to the display device 105 (e.g., as a notification, alert, or alarm). In some embodiments, in step 2424, the display device 105 may display an appropriate indication of the prediction of the amount of time remaining before sensor EOL. In some embodiments, the display device 105 may use a color (e.g., blue, yellow, or red) to indicate a level of severity (e.g., low, intermediate, or high) with respect to how close the sensor 100 is to the predicted end of life.

In some embodiments, the process 2400 may include a step 2426 in which the transmitter 101 assesses the performance of the analyte sensor 100. In some non-limiting embodiments, the transmitter 101 may assess sensor performance by calculating an MSP for the sensor 100.

In some embodiments, the process 2400 may include a step 2428 in which the transmitter 101 may issue a sensor retirement alarm. In some non-limiting embodiments, in response to a sensor retirement alarm, the transmitter 101 may do one or more of the following: (i) convey the sensor retirement alarm to the display device 105 and (ii) blind the sensor output (i.e., stop conveying calculated analyte concentrations to the display device 105 for display). In some embodiments, in response to receiving the sensor retirement alarm, the display device 105 may display an indication that the sensor needs to be replaced and/or that analyte concentrations will not be displayed until the after the sensor is replaced.

Figure 23:
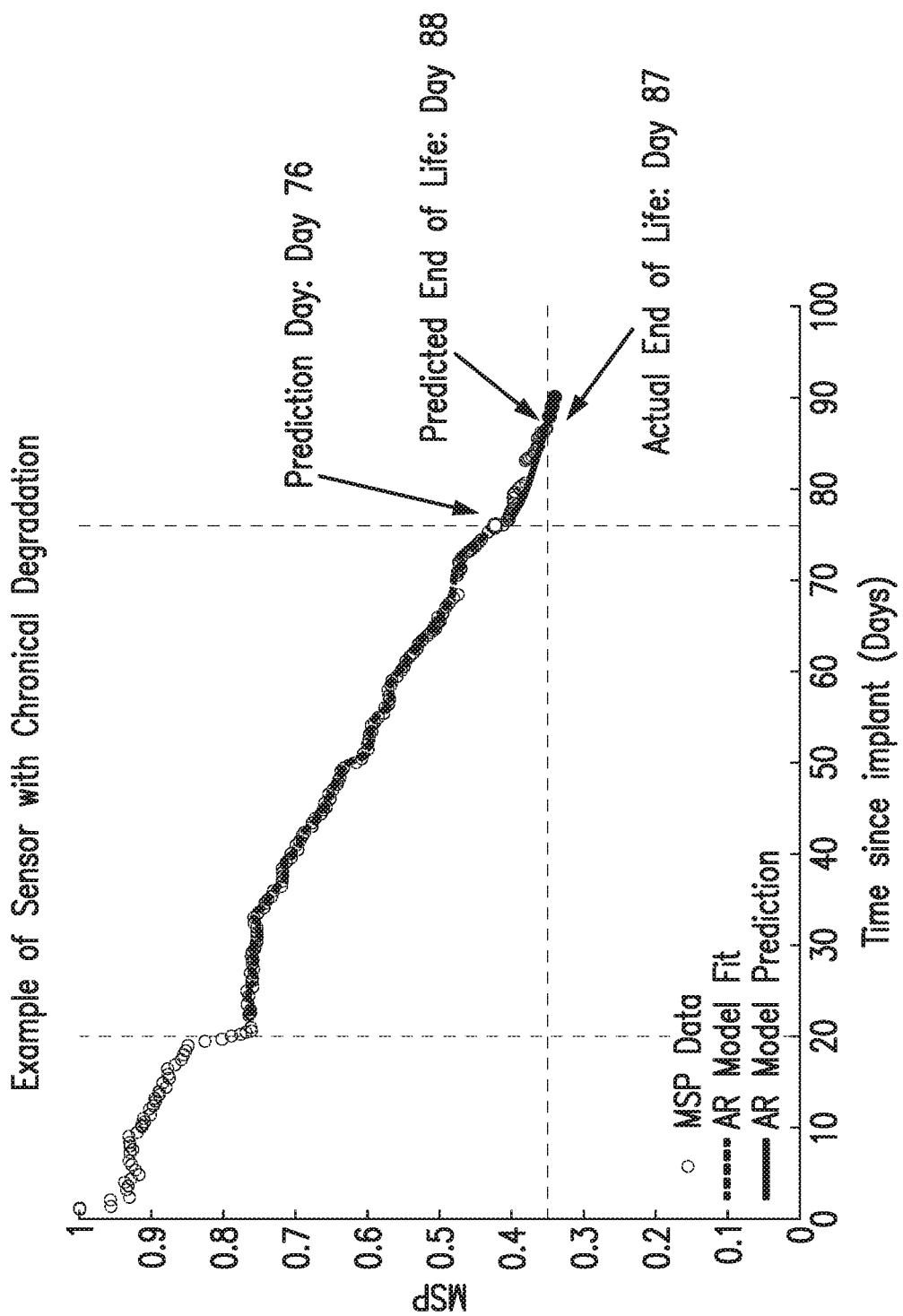
FIG. 23 is a graph illustrating a non-limiting example of MSP data, AR model fit, AR model prediction, predicted EOL, and actual EOL for an implanted sensor in accordance with embodiments of the present invention.

FIG. 23 is a graph illustrating a non-limiting example of MSP data, AR model fit, AR model prediction, predicted EOL, and actual EOL for an implanted sensor 100. In the example, an MSP deficiency threshold of 0.35 was used as the cutoff for when the performance of a sensor 100 is determined (or predicted) to be deficient. In the example illustrated in FIG. 23, the sensor performance degraded chronically or smoothly. On day 76, analyte monitoring system predicted that EOL would occur on day 88 (i.e., predicted that MSP would cross the MSP deficiency threshold of 0.35 on day 88), and the actual EOL occurred on day 87 (i.e., the sensor performance was determined to be deficient because, for example, MSP went below the MSP deficiency threshold for at least 3600 seconds). However, sensor performance for some sensors may degrade in a burst or abruptly (as opposed to smoothly). In some embodiments, the EOL prediction error may be within +/−3 days if the MSP has a smooth decay. However, either the prediction error or the prediction window (i.e., days between the prediction day and the actual sensor EOL) may increase if the MSP decay rate changes drastically.

In some non-limiting embodiments, the AR model may be used to update one or more of the first, second, and third performance thresholds associated with the first, second, and third amounts of time remaining before sensor EOL, respectively, and discussed above with respect to the process 900 illustrated in FIG. 8.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For instance, although aspects of the invention have been described above with respect to predicting the end of the life of an analyte sensor in an analyte monitoring system, in some alternative embodiments, the end of life prediction of the present invention may be applied to different devices (e.g., a temperature sensor, an insulin pump, or a pacemaker) in different systems (e.g., temperature monitoring systems, insulin delivery systems, or cardiac contraction control systems). Also, although examples of particular parameters, thresholds, and time periods used in the sensor performance assessment, sensor performance deficiency determination, sensor delamination detection, and end of life prediction have been described above, the parameters, thresholds, and time periods may vary from one embodiment to the next, and different parameters, thresholds, and time periods may be used for different sensors and/or system configurations.

In addition, although in some embodiments the transmitter 101 of the analyte monitoring system 50 performs one or more of the sensor performance assessment, sensor performance deficiency determination, sensor delamination detection, and end of life prediction, this is not required. In some alternative embodiments, portions of or all of the sensor performance assessment, sensor performance deficiency determination, sensor delamination detection, and end of life prediction may be performed by one or more of the analyte sensor 100 and display device 105.

Moreover, although some embodiments have been described as using an AR model, this is not required. Some alternative embodiments may use a different model, such as, for example and without limitation, linear regression, multivariate adaptive regression splines (MARS), exponential decay model, AR model with regularization, a fitted linear model, a non-linear (polynomial) model, or other predictive model defined by statically or analytically derived expressions.

What is claimed is:

1. An analyte monitoring system comprising:
an analyte sensor including an indicator element that exhibits one or more detectable properties based on an amount or concentration of an analyte in proximity to the indicator element; and
a transmitter comprising a sensor interface device and a controller, and the transmitter is configured to:
(i) use the sensor interface device to receive measurement information from the analyte sensor,
(ii) use the controller to use at least the received measurement information to calculate two or more measures selected from the group consisting of:
(a) a responsiveness of the indicator element of the analyte sensor to changes in an amount or concentration of the analyte in proximity to the indicator element,
(b) a strength of the one or more detectable properties exhibited by the indicator element of the analyte sensor,
(c) an accuracy of the analyte sensor, and
(d) a response of a body in which the analyte sensor is located to the analyte sensor,
(iii) use the controller to calculate a minimum value of the calculated two or more measures,
(iv) determine whether a performance of the analyte sensor is deficient based at least on the calculated minimum value, and
(v) predict an amount of time remaining before the performance of the analyte sensor becomes deficient based on at least the calculated minimum value.

2. The analyte monitoring system of claim 1, wherein the transmitter is further configured to receive one or more reference measurements, and the transmitter is configured to use at least the measurement information and the one or more reference measurements to calculate the two or more measures.

3. The analyte monitoring system of claim 1, wherein one or more of the responsiveness, the strength, the accuracy, and the response of the body is weighted.

4. The analyte monitoring system of claim 1, wherein the transmitter is configured to, in determining whether the performance of the analyte sensor is deficient, compare the calculated minimum value to a deficiency threshold.

5. The analyte monitoring system of claim 1, wherein the transmitter is configured to, in determining whether the performance of the analyte sensor is deficient, determine whether the calculated minimum value is below a deficiency threshold for at least a period of time.

6. The analyte monitoring system of claim 1, wherein the calculated minimum value is an assessment of the performance of the analyte sensor, and the transmitter is configured to, in predicting the amount of time remaining before the performance of the analyte sensor becomes deficient, train an autoregressive model using one or more assessments of the performance of the analyte sensor and using the trained autoregressive model to predict future performance of the analyte sensor.

7. The analyte monitoring system of claim 6, wherein the transmitter is configured to, in predicting the amount of time remaining before the performance of the analyte sensor becomes deficient, compare the predicted future performance of the analyte sensor to a deficiency threshold, and the predicted amount of time remaining before the performance of the analyte sensor becomes deficient is based on when the predicted future performance of the analyte sensor crosses the deficiency threshold.

8. The analyte monitoring system of claim 1, wherein the transmitter is configured to, in predicting the amount of time remaining before the performance of the analyte sensor becomes deficient, compare the calculated minimum value to a first sensor performance threshold and predict that a first amount of time remains before the performance of the analyte sensor becomes deficient when the calculated minimum value is less than the first sensor performance threshold.

9. The analyte monitoring system of claim 8, wherein the transmitter is configured to, in predicting the amount of time remaining before the performance of the analyte sensor becomes deficient, compare the calculated minimum value to a second sensor performance threshold and predict that a second amount of time remains before the performance of the analyte sensor becomes deficient when the calculated minimum value is less than the second sensor performance threshold.

10. The analyte monitoring system of claim 9, wherein the second amount of time is less than the first amount of time, and the second sensor performance threshold is less than the first sensor performance threshold.

11. The analyte monitoring system of claim 1, wherein the transmitter is configured to, in predicting the amount of time remaining before the performance of the analyte sensor becomes deficient, compare a time since the analyte sensor was implanted to a first implant time threshold and predict that a first amount of time remains before the performance of the analyte sensor becomes deficient when the time since the analyte sensor was implanted is greater than the first implant time threshold.

12. The analyte monitoring system of claim 11, wherein the transmitter is configured to, in predicting the amount of time remaining before the performance of the analyte sensor becomes deficient, compare a time since the analyte sensor was implanted to a second implant time threshold and predicting that a second amount of time remains before the performance of the analyte sensor becomes deficient when the time since the analyte sensor was implanted is greater than the second implant time threshold.

13. The analyte monitoring system of claim 12, wherein the second amount of time is less than the first amount of time, and the second implant time threshold is greater than the first implant time threshold.

14. The analyte monitoring system of claim 1, further comprising a display device comprising a display, wherein the display device is configured to (i) receive the predicted amount of time remaining before the performance of the analyte sensor becomes deficient from the transmitter and (ii) display the predicted amount of time remaining before the performance of the analyte sensor becomes deficient.

15. The analyte monitoring system of claim 14, wherein the display device is configured to use a color to indicate a level of severity with respect to the predicted amount of time remaining before the performance of the analyte sensor becomes deficient.

16. The analyte monitoring system of claim 1, wherein the transmitter is further configured to detect sensor delamination based on at least the measurement information.

17. A method comprising:
using an indicator element of an analyte sensor to exhibit one or more detectable properties based on an amount or concentration of an analyte in proximity to the indicator element;
using a sensor interface device of a transmitter to receive measurement information from the analyte sensor;
using a controller of the transmitter to use at least the received measurement information to calculate two or more measures selected from the group consisting of:
(a) a responsiveness of the indicator element of the analyte sensor to changes in an amount or concentration of the analyte in proximity to the indicator element,
(b) a strength of the one or more detectable properties exhibited by the indicator element of the analyte sensor,
(c) an accuracy of the analyte sensor, and
(d) a response of a body in which the analyte sensor is located to the analyte sensor;
using the controller of the transmitter to calculate a minimum value of the calculated two or more measures;
using the transmitter to determine whether the performance of the analyte sensor is deficient based at least on the calculated minimum value; and, if not deficient
using the transmitter to predict an amount of time remaining before the performance of the analyte sensor becomes deficient based on at least the calculated minimum value.

* * * * *